United States Patent
Lindsey et al.

(10) Patent No.: US 6,559,374 B2
(45) Date of Patent: *May 6, 2003

(54) TRANS BETA SUBSTITUTED CHLORINS AND METHODS OF MAKING AND USING THE SAME

(75) Inventors: Jonathan S. Lindsey, Raleigh, NC (US); Thiagarajan Balasubramanian, Raleigh, NC (US)

(73) Assignee: North Carolina State University, Raleigh, NC (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/852,560

(22) Filed: May 10, 2001

(65) Prior Publication Data

US 2002/0033192 A1 Mar. 21, 2002

Related U.S. Application Data

(63) Continuation-in-part of application No. 09/670,463, filed on Sep. 26, 2000, which is a continuation-in-part of application No. 09/621,797, filed on Jul. 21, 2000, now Pat. No. 6,420,648.

(51) Int. Cl.[7] ............... H01L 31/0248; H01L 31/04; C07D 487/22
(52) U.S. Cl. ............... 136/263; 136/256; 136/252; 257/40; 257/431; 429/111; 429/213; 540/145; 540/460; 514/410
(58) Field of Search .................. 136/263, 256, 136/252; 257/40, 431; 429/111, 213; 540/145, 460; 514/410

(56) References Cited

U.S. PATENT DOCUMENTS

| | | | | |
|---|---|---|---|---|
| 5,004,611 A | * | 4/1991 | Bommer et al. ........... 540/145 |
| 5,004,811 A | | 4/1991 | Bommer et al. | |
| 5,093,349 A | * | 3/1992 | Pandey et al. ............. 514/410 |
| 5,145,863 A | * | 9/1992 | Dougherty et al. ......... 514/410 |
| 5,330,741 A | * | 7/1994 | Smith et al. .............. 424/9.61 |
| 5,780,622 A | * | 7/1998 | Dolphin et al. ............ 540/472 |
| 5,831,088 A | * | 11/1998 | DOlphin et al. ........... 540/474 |
| 6,147,207 A | * | 11/2000 | Sinn et al. ................ 540/145 |
| 6,376,483 B1 | * | 4/2002 | Robinson ................. 514/185 |
| 6,407,330 B1 | | 6/2002 | Lindsey et al. | |
| 6,420,648 B1 | | 7/2002 | Lindsey et al. | |

OTHER PUBLICATIONS

Smith et al, "Syntheses of Heme d Models," J. Am. Chem. Soc., vol. 106, pp. 5746–5748, (1984).*

Burns et al, "Synthesis of Chlorins from Unsymmetrically Substituted Iron Porphyrins," J. Chem. Soc., Perkin Trans. 1, pp. 3119–3131, (1988).*

Balasubramanian et al, "Rational Synthesis of beta–Substituted Chlorin Building Blocks," J. Org, Chem., vol. 65, pp. 7919–7929, Oct. 21, 2000.*

Kamogawa, Kiroyoshi, *Preparatino of Chlorophyll Polymer*, Polymer Letters, vol. 10, pp. 711–713 (1972).

Balasubramanian, Thiagarajan, et al., *Rational Synthesis of δ–Substituted Chlorin Building Blocks*, J. Org. Chem., vol. 65, pp. 7919–7929 (2000).

International Search Report, International Application No. PCT/US01/22986 dated Dec. 28, 2001.

* cited by examiner

*Primary Examiner*—Alan Diamond
(74) *Attorney, Agent, or Firm*—Myers Bigel Sibley & Sajovec

(57) ABSTRACT

Trans beta substituted chlorins and methods of making the same are disclosed, along with polymers formed from or containing such trans beta substituted chlorins as one or more monomeric units therein, light harvesting rods formed from such polymers, and electrodes carrying such polymers.

32 Claims, 19 Drawing Sheets

TRANS-CHLORINS WITH TWO β SUBSTITUENTS

I          II

TRANS-CHLORINS WITH TWO MESO SUBSTITUENTS

III          IV

CHLORIN NOMENCLATURE SHOWING IUPAC-IUB RING LABELS A-D

FREE BASE CHLORIN            METALLOCHLORIN

ORIENTATION OF THE TRANSITION DIPOLE
MOMENT OF THE LONG-WAVELENGTH
ABSORPTION BAND

CHLORIN HOMO $a_2$ MO

NEW WESTERN HALF    NEW EASTERN HALF

TRANS-CHLORIN BUILDING BLOCK WITH TWO β SUBSTITUENTS (M = A DIVALENT METAL OR TWO PROTONS)

TRANS-CHLORIN BUILDING BLOCKS WITH TWO β SUBSTITUENTS
(M = A DIVALENT METAL OR TWO PROTONS)

$J^1$—L—BB—L—$J^2$  +  $J^3$—L—BB—L—$J^4$

| $J^2$ | $J^3$ | REACTION TYPE |
|---|---|---|
| -B(OH)$_2$ | -Cl, -Br, I | SUZUKI |
| ≡—H | -Cl, -Br, I | SONOGASHIRA |
| ≡—H | ≡—H | GLASER |
| ≡—H | ≡—X | CADIOT-CHODKIEWICZ |
| -CHO | -Br, I | WITTIG |
| —HC=CH$_2$ | -Br, I | HECK |

*FIG. 11*

β-SUBSTITUTED WESTERN HALF

TRANS BETA SUBSTITUTED CHLORINS AND METHODS OF MAKING AND USING THE SAME

RELATED APPLICATIONS

This application is a continuation in part of commonly owned application Ser. No. 09/670,463, filed Sep. 26, 2000 pending, which is a continuation in part of Ser. No. 09/621797, filed Jul. 21, 2000, now U.S. Pat. No. 6,420,648 the disclosures of both of which are incorporated by reference herein in their entirety.

GOVERNMENT SUPPORT

This invention was made with Government support under Grant No. DE-FG02-96 ER14632 from the Department of Energy and Grant No. GM36238 from the National Institutes of Health. The Government has certain rights to this invention.

FIELD OF THE INVENTION

The present invention concerns solar cells, particularly regenerative solar cells, and light harvesting arrays useful in such solar cells.

BACKGROUND OF THE INVENTION

Molecular approaches for converting sunlight to electrical energy have a rich history with measurable "photoeffects" reported as early as 1887 in Vienna (Moser, J. *Montash. Chem.* 1887, 8, 373.). The most promising designs were explored in considerable detail in the 1970's (Gerischer, H. *Photochem. Photobiol.* 1972, 16, 243; Gerischer, *H. Pure Appl. Chem.* 1980, 52, 2649; Gerischer, H.; Willig, F. *Top. Curr. Chem.* 1976, 61, 31). Two common approaches are shown in FIG. 1, both of which incorporate molecules that selectively absorb sunlight, termed photosensitizers or simply sensitizers (S), covalently bound to conductive electrodes. Light absorption by the sensitizer creates an excited state, S*, that injects an electron into the electrode and then oxidizes a species in solution. The right hand side depicts a simplified *photoelectrosynthetic cell*. This cell produces both electrical power and chemical products. Many of the molecular approaches over the past few decades were designed to operate in the manner shown with the goal of splitting water into hydrogen and oxygen. Shown on the left hand side is a regenerative cell that converts light into electricity with no net chemistry. In the regenerative solar cell shown, the oxidation reactions that take place at the photoanode are reversed at the dark cathode.

The principal difficulty with these solar cell designs is that a monolayer of a molecular sensitizer on a flat surface does not absorb a significant fraction of incident visible light. As a consequence, even if the quantum yields of electron transfer are high on an absorbed photon basis, the solar conversion efficiency will be impractically low because so little light is absorbed. Early researchers recognized this problem and tried to circumvent it by utilizing thick films of sensitizers. This strategy of employing thick absorbing layers was unsuccessful as intermolecular excited-state quenching in the thick sensitizer film decreased the yield of electron injection into the electrode.

One class of thick film sensitizers is provided by the so-called organic solar cells (Tang, C. W. and Albrecht, A. C. *J. Chem. Phys.* 1975, 63, 953–961). Here a 0.01 to 5 µm thick film, typically comprised of phthalocyanines, perylenes, chlorophylls, porphyrins, or mixtures thereof, is deposited onto an electrode surface and is employed in wet solar cells like those shown, or as solid-state devices where a second metal is deposited on top of the organic film. The organic layer is considered to be a small bandgap semiconductor with either n-or p-type photoconductivity and the proposed light-to-electrical energy conversion mechanisms incorporate excitonic energy transfer among the pigments in the film toward the electrode surface where interfacial electron transfer takes place. However, the importance of these proposed mechanistic steps is not clear. Increased efficiencies that result from vectorial energy transfer among the pigments have not been convincingly demonstrated. Furthermore, the reported excitonic diffusion lengths are short relative to the penetration depth of the light. Accordingly, most of the light is absorbed in a region where the energy cannot be translated to the semiconductor surface. The excitons are also readily quenched by impurities or incorporated solvent, leading to significant challenges in reproducibility and fabrication. The state-of-the-art organic solar cells are multilayer organic "heterojunction" films or doped organic layers that yield 2% efficiencies under low irradiance, but the efficiency drops markedly as the irradiance approaches that of one sun (Forrest, S. R. et al., *J. Appl. Phys.* 1989, 183, 307; Schon, J. H. et al., *Nature* 2000, 403, 408).

Another class of molecular-based solar cells are the so-called photogalvanic cells that were the hallmark molecular level solar energy conversion devices of the 1940's –1950's (Albery, W. J. *Acc. Chem. Res.* 1982, 15, 142). These cells are distinguished from those discussed above in that the excited sensitizer does not undergo interfacial electron transfer. The cells often contain sensitizers embedded in a membrane that allows ion transfer and charge transfer; the membrane physically separates two dark metal electrodes and photogenerated redox equivalents. The geometric arrangement precludes direct excited-state electron transfer from a chromophore to or from the electrodes. Rather, intermolecular charge separation occurs and the reducing and oxidizing equivalents diffuse to electrodes where thermal interfacial electron transfer takes place. A transmembrane Nernst potential can be generated by photodriven electron transfer occurring in the membrane. In photoelectrosynthetic galvanic cells, chemical fuels may be formed as well. This general strategy for dye sensitization of electrodes has been employed in many guises over the years, but the absolute efficiencies remain very low. Albery concluded that an efficiency of ~13% theoretically could be achieved in an aqueous regenerative photogalvanic cell. However, efficiencies realized to date are typically less than 2%.

In 1991, a breakthrough was reported by Gratzel and O'Regan (O'Regan, B. et al., *J. Phys. Chem.* 1990, 94, 8720; O'Regan, B. and Gratzel, M. *Nature* 1991, 353, 737). By replacing the planar electrodes with a thick porous colloidal semiconductor film, the surface area for sensitizer binding increased by over 1000-fold. Gratzel and O'Regan demonstrated that a monolayer of sensitizer coating the semiconductor particles resulted in absorption of essentially all of the incident light, and incident photon-to-electron energy conversion efficiencies were unity at individual wavelengths of light in regenerative solar cells. Furthermore, a global efficiency of ~5% was realized under air-mass 1.5 illumination conditions; this efficiency has risen to a confirmed 10.69% today (Gratzel, M. in "Future Generation Photovoltaic Technologies" McConnell, R. D.; AIP Conference Proceedings 404, 1997, page 119). These "Gratzel" solar cells have already found niche markets and are commercially available in Europe.

These high surface area colloidal semiconductor films (Gratzel cells) achieve a high level of absorption but also have the following significant drawbacks. (1) A liquid junction is required for high efficiency (because the highly irregular surface structure makes deposition of a solid-state conductive layer essentially impossible). (2) The colloidal semiconductor films require high temperature annealing steps to reduce internal resistances. Such high temperatures impose severe limitations on the types of conductive substrates that can be used. For example, polymeric substrates that melt below the required annealing temperatures cannot be used. (3) Significant losses are associated with transporting charge through the thick semiconductor films. These losses do not appreciably decrease the photocurrent, but have a large effect on the voltage output and thus the power is decreased significantly (Hagfeldt, A.; Gratzel, M. *Chem. Rev.* 1995, 95, 49). Accordingly, there remains a need for new molecular approaches to the construction of solar cells.

SUMMARY OF THE INVENTION

The present invention provides, among other things, trans-substituted chlorins and methods of making such trans substituted chlorins. The trans-substituted chlorins may be used, among other things, as building blocks in polymers that may be incorporated into light harvesting arrays and solar cells described herein.

A light harvesting array of the present invention is useful, among other things, for the manufacture of solar cells. The light harvesting array comprises:

(a) a first substrate comprising a first electrode; and
(b) a layer of light harvesting rods electrically coupled to the first electrode, each of the light harvesting rods comprising a polymer of Formula I:

  (I)

wherein:
m is at least 1, and may be from two, three or four to 20 or more;
$X^1$ is a charge separation group having an excited-state of energy equal to or lower than that of $X^2$; and
$X^2$ through $X^{m+1}$ are chromophores.

In light harvesting rods of Formula I herein, $X^1$ preferably comprises a porphyrinic macrocycle, which may be in the form of a double-decker sandwich compound. Further, $X^2$ through $X^{m+1}$ also preferably comprise porphyrinic macrocycles.

In preferred embodiments of the light harvesting rods of Formula I herein, at least one of (e.g., two, three, a plurality of, the majority of or all of) $X^1$ through $X^{m+1}$ is/are selected from the group consisting of chlorins, bacteriochlorins, and isobacteriochlorins, and most preferably is a trans-substituted chlorin as described herein.

Light-harvesting arrays provide intense absorption of light and deliver the resulting excited state to a designated location within the molecular array. There are a variety of applications of light-harvesting arrays. Light-harvesting arrays can be used as components of low-level light detection systems, especially where control is desired over the wavelength of light that is collected. Light-harvesting arrays can be used as input elements in optoelectronic devices, and as an input unit and energy relay system in molecular-based signaling systems. One application of the latter includes use in molecular-based fluorescence sensors. The molecular-based sensor employs a set of probe groups (which bind an analyte) attached to a molecular backbone that undergoes excited-state energy transfer. The binding of a single analyte to any one of the probe groups yields a complex that can quench the excited state that freely migrates along the backbone (i.e., exciton). The quenching phenomenon results in diminished fluorescence from the molecular backbone. Because only one bound analyte can cause the quenching phenomenon, the sensitivity is much higher than if there was a 1:1 ratio of probe groups and fluorescence groups. Previously, such molecular-based fluorescence sensors have employed UV or near-UV absorbing chromophores in the molecular backbone. The light-harvesting arrays described herein are ideally suited as components for a new class of molecular-based fluorescence sensors that absorb (and fluoresce) strongly in the visible and near-infrared region.

A particular application of the light-harvesting arrays described herein is in solar cells. A solar cell as described herein typically comprises:

(a) a first substrate comprising a first electrode;
(b) a second substrate comprising a second electrode, with the first and second substrate being positioned to form a space therebetween, and with at least one of (i) the first substrate and the first electrode and (ii) the second substrate and the second electrode being transparent;
(c) a layer of light harvesting rods electrically coupled to the first electrode, each of the light harvesting rods comprising a polymer of Formula I:

  (I)

wherein:
m is at least 1 (and typically two, three or four to twenty or more);
$X^1$ is a charge separation group having an excited-state of energy equal to or lower than that of $X^2$;
$X^2$ through $X^{m+1}$ are chromophores; and
$X^1$ is electrically coupled to the first electrode; the solar cell further comprising
(d) an electrolyte in the space between the first and second substrates. A mobile charge carrier can optionally be included in the electrolyte.

In preferred embodiments of the solar cells described herein, at least one of (e.g., two, three, a plurality of, the majority of or all of) $X^1$ through $X^{m+1}$ is/are selected from the group consisting of chlorins, bacteriochlorins, and isobacteriochlorins, and most preferably is a trans-substituted chlorin as described herein.

A variety of different electrical devices comprised of a solar cell as described above having circuits (typically resistive loads) electrically coupled thereto can be produced with the solar cells of the invention, as discussed in greater detail below.

The present invention is explained in greater detail in the drawings herein and the specification set forth below.

BRIEF DESCRIPTION OF THE DRAWINGS

FIG. 11 illustrates reactions suitable for preparing light-harvesting rod oligomers.

DETAILED DESCRIPTION OF THE PREFERRED EMBODIMENTS

Figure 1:
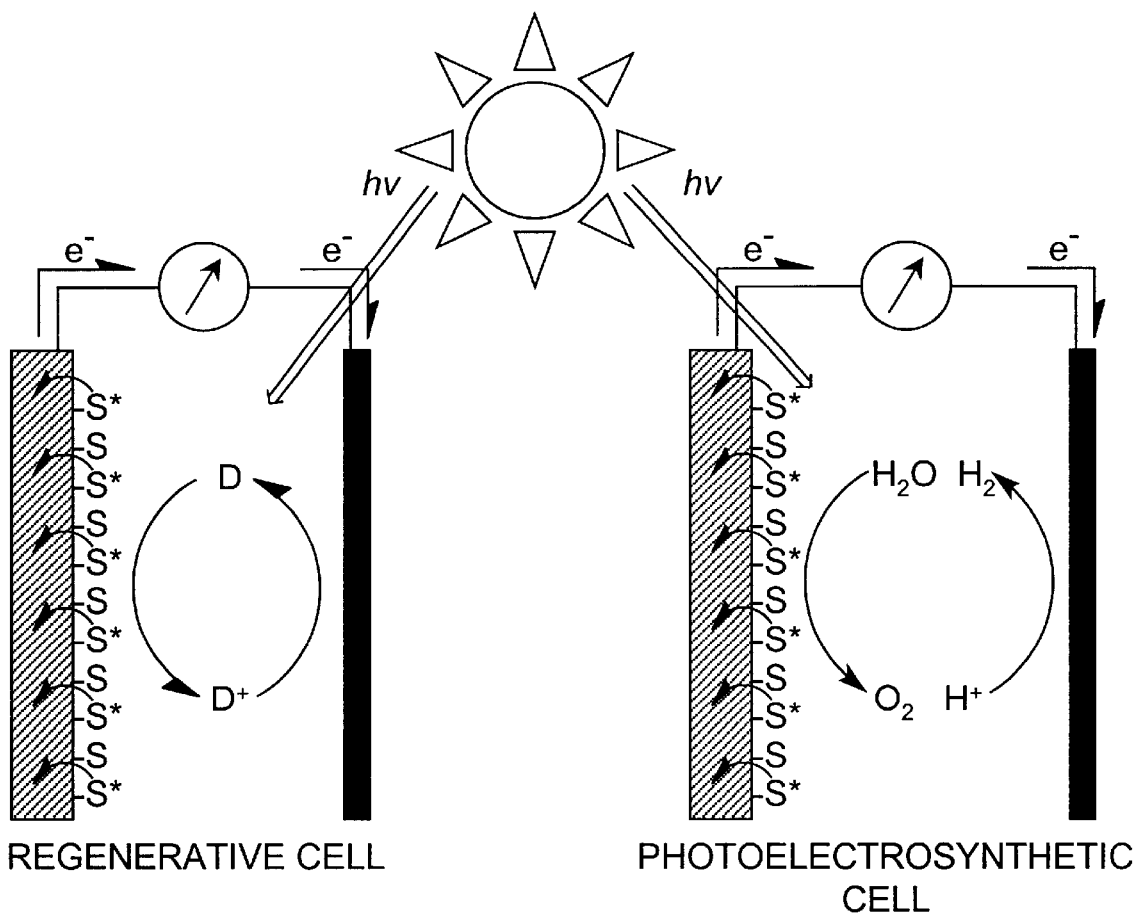
FIG. 1. Diagrams of the two common molecular approaches for light to electrical energy conversion.

The following terms and phrases are used herein:

A substrate as used herein is preferably a solid material (which may be flexible or rigid) suitable for the attachment of one or more molecules. Substrates can be formed of materials including, but not limited to glass, organic polymers, plastic, silicon, minerals (e.g. quartz), semiconducting materials, ceramics, metals, etc. The substrate may be in any suitable shape, including flat, planar, curved, rod-shaped, etc. The substrate may be inherently conductive and serve itself as an electrode, or an electrode may be formed on or connected to the substrate by any suitable means (e.g., deposition of a gold layer or a conductive oxide layer). Either or both of the substrates in the solar cells may be transparent (that is, wavelengths of light that excite the chromophores can pass through the substrate and corresponding electrode, even if they are visually opaque). In light-harvesting arrays, the substrate and electrode may be of any suitable type. One of the substrates may be opaque with respect to the wavelengths of light that excite the chromophores. One of the substrates may be reflective or provided with a reflective coating so that light that passes through the arrays or rods is reflected back to the arrays or rods.

The term "electrode" refers to any medium capable of transporting charge (e.g. electrons) to and/or from a light harvesting rod. Preferred electrodes are metals (e.g., gold, aluminum), non-metals (e.g., conductive oxides, carbides, sulfide, selinides, tellurides, phosphides, and arsenides such as cadmium sulfide, cadmium telluride, tungsten diselinide, gallium arsenide, gallium phosphide, etc.), and conductive organic molecules. The electrodes can be manufactured to virtually any 2-dimensional or 3-dimensional shape.

The term "conductive oxide" as used herein refers to any suitable conductive oxide including binary metal oxides such as tin oxide, indium oxide, titanium oxide, copper oxide, and zinc oxide, or ternary metal oxides such as strontium titanate and barium titanate. Other examples of suitable conductive oxides include but are not limited to indium tin oxide, titanium dioxide, tin oxide, gallium indium oxide, zinc oxide, and zinc indium oxide. The metal oxide semiconductors may be intrinsic or doped, with trace amounts of materials, to control conductivity.

The term "heterocyclic ligand" as used herein generally refers to any heterocyclic molecule consisting of carbon atoms containing at least one, and preferably a plurality of, hetero atoms (e.g., N, O, S, Se, Te), which hetero atoms may be the same or different, and which molecule is capable of forming a sandwich coordination compound with another heterocyclic ligand (which may be the same or different) and a metal. Such heterocyclic ligands are typically macrocycles, particularly tetrapyrrole derivatives such as the phthalocyanines, porphyrins, and porphyrazines The term "porphyrinic macrocycle" refers to a porphyrin or porphyrin derivative. Such derivatives include porphyrins with extra rings ortho-fused, or ortho-perifused, to the porphyrin nucleus, porphyrins having a replacement of one or more carbon atoms of the porphyrin ring by an atom of another element (skeletal replacement), derivatives having a replacement of a nitrogen atom of the porphyrin ring by an atom of another element (skeletal replacement of nitrogen), derivatives having substituents other than hydrogen located at the peripheral (meso-,β-) or core atoms of the porphyrin, derivatives with saturation of one or more bonds of the porphyrin (hydroporphyrins, e.g., chlorins, bacteriochlorins, isobacteriochlorins, decahydroporphyrins, corphins, pyrrocorphins, etc.), derivatives obtained by coordination of one or more metals to one or more porphyrin atoms (metalloporphyrins), derivatives having one or more atoms, including pyrrolic and pyrromethenyl units, inserted in the porphyrin ring (expanded porphyrins), derivatives having one or more groups removed from the porphyrin ring (contracted porphyrins, e.g., corrin, corrole) and combinations of the foregoing derivatives (e.g phthalocyanines, porphyrazines, naphthalocyanines, subphthalocyanines, and porphyrin isomers). Preferred porphyrinic macrocycles comprise at least one 5-membered ring.

The term porphyrin refers to a cyclic structure typically composed of four pyrrole rings together with four nitrogen atoms and two replaceable hydrogens for which various metal atoms can readily be substituted. A typical porphyrin is hemin.

A "chlorin" is essentially the same as a porphyrin, but differs from a porphyrin in having one partially saturated pyrrole ring. The basic chromophore of chlorophyll, the green pigment of plant photosynthesis, is a chlorin.

A "bacteriochlorin" is essentially the same as a porphyrin, but differs from a porphyrin in having two partially saturated non-adjacent (i.e., trans) pyrrole rings.

An "isobacteriochlorin" is essentially the same as a porphyrin, but differs from a porphyrin in having two partially saturated adjacent (i.e., cis) pyrrole rings.

The terms "sandwich coordination compound" or "sandwich coordination complex" refer to a compound of the formula $L_n M^{n-1}$, where each L is a heterocyclic ligand such as a porphyrinic macrocycle, each M is a metal, n is 2 or more, most preferably 2 or 3, and each metal is positioned between a pair of ligands and bonded to one or more hetero atom (and typically a plurality of hetero atoms, e.g., 2, 3, 4, 5) in each ligand (depending upon the oxidation state of the metal). Thus sandwich coordination compounds are not organometallic compounds such as ferrocene, in which the metal is bonded to carbon atoms. The ligands in the sandwich coordination compound are generally arranged in a stacked orientation (i.e., are generally cofacially oriented and axially aligned with one another, although they may or may not be rotated about that axis with respect to one another). See, e.g., D. Ng and J. Jiang, *Chem. Soc. Rev.* 26, 433–442 (1997). Sandwich coordination compounds may be "homoleptic" (wherein all of the ligands L are the same) or "heteroleptic" (wherein at least one ligand L is different from the other ligands therein).

The term "double-decker sandwich coordination compound" refers to a sandwich coordination compound as described above where n is 2, thus having the formula $L^1-M^1-L^2$, wherein each of $L^1$ and $L^2$ may be the same or different. See, e.g., J. Jiang et al., *J. Porphyrins Phthalocyanines* 3, 322–328 (1999).

The term "multiporphyrin array" refers to a discrete number of two or more covalently-linked porphyrinic macrocycles. The multiporphyrin arrays can be linear, cyclic, or branched, but are preferably linear herein. Light harvesting rods herein are preferably multiporphyrin arrays. The light harvesting rods or multiporphyrin arrays may be linear (that is, all porphyrinic macrocycles may be linked in trans) or may contain one or more bends or "kinks" (for example, by including one or more non-linear linkers in a light-harvesting rod, or by including one or more cis-substituted porphyrinic macrocycles in the light harvesting rod) Some of the porphyrinic macrocycles may further include additional ligands, particularly porphyrinic macrocycles, to form sandwich coordination compounds as described further below. The rods optionally but preferably are oriented substantially perpendicularly to either, and most preferably both, of the first and second electrodes.

"Chromophore" means a light-absorbing unit which can be a unit within a molecule or can comprise the entire molecule. Typically a chromophore is a conjugated system (alternating double and single bonds which can include non-bonded electrons but is not restricted to alternating double and single bonds since triple and single bonds, since mixtures of alternating triple/double and single bonds also constitute chromophores. A double or triple bond alone constitutes a chromophore. Heteroatoms can be included in a chromophore.). Examples of chromophores include the cyclic 18 pi-electron conjugated system that imparts color to porphyrinic pigments, the linear system of alternating double and single bonds in the visual pigment retinal, or the carbonyl group in acetone.

"Charge separation group" and "charge separation unit" refer to molecular entities that upon excitation (by direct absorption or energy transfer from another absorber) displace an electron to another part of the same molecule, or transfer an electron to a different molecule, semiconductor, or metal. The "charge separation group" and "charge separation unit" results in storage of some fraction of the excited state energy upon displacement or transfer of an electron. Typically the "charge separation group" and "charge separation unit" is located at the terminus of a light-harvesting array or rod, from which excited-state energy is received. The "charge separation group" and "charge separation unit" facilitates or causes conversion of the excited-state energy into a separate electron and hole or an electron-hole pair. The electron can be injected into the semiconductor by the "charge separation group" or "charge separation unit". It is feasible that the "charge separation group" and "charge separation unit" could extract an electron from a different molecule or semiconductor, thereby creating a negative charge on the "charge separation group" and "charge separation unit" and a hole in the other molecule or semiconductor. The reaction center of bacterial photosynthesis is a premier example of a "charge separation group" or "charge separation unit". Synthetic porphyrin-quinone or porphyrin-buckyball molecules also function to absorb light and utilize the resulting energy to separate charge.

The term "substituent" as used in the formulas herein, particularly designated by S or $S^n$ where n is an integer, in a preferred embodiment refer to electron-rich or electron-deficient groups (subunits) that can be used to adjust the redox potential(s) of the subject compound. Preferred substituents include, but are not limited to, H, aryl, phenyl, cycloalkyl, alkyl, alkenyl, alkynyl, halogen, alkoxy, alkylthio, perfluoroalkyl, perfluoroaryl, pyridyl, cyano, thiocyanato, nitro, amino, alkylamino, acyl, sulfoxyl, sulfonyl, amido, and carbamoyl. In certain embodiments, a substituted aryl group is attached to a porphyrin or a porphyrinic macrocycle, and the substituents on the aryl group are selected from the group consisting of aryl, phenyl, cycloalkyl, alkyl, alkenyl, alkynyl, halogen, alkoxy, alkylthio, perfluoroalkyl, perfluoroaryl, pyridyl, cyano, thiocyanato, nitro, amino, alkylamino, acyl, sulfoxyl, sulfonyl, amido, and carbamoyl. Additional substituents include, but are not limited to, 4-chlorophenyl, 4-trifluoromethylphenyl, and 4-methoxyphenyl. Preferred substituents provide a redox potential range of less than about 5 volts, preferably less than about 2 volts, more preferably less than about 1 volt.

The term "aryl" refers to a compound whose molecules have the ring structure characteristic of benzene, naphthalene, phenanthrene, anthracene, etc. (i.e., either the 6-carbon ring of benzene or the condensed 6-carbon rings of the other aromatic derivatives). For example, an aryl group may be phenyl ($C_6H_5$) or naphthyl ($C_{10}H_7$). It is recognized that the aryl group, while acting as substituent can itself have additional substituents (e.g. the substituents provided for $S^n$ in the various formulas herein).

The term "alkyl" refers to a paraffinic hydrocarbon group, typically C1 to C4, which may be derived from an alkane by dropping one hydrogen from the formula. Examples are methyl ($CH_3$—), ethyl ($C_2H_5$—), propyl ($CH_3CH_2CH_2$—), isopropyl (($CH_3)_2CH$—).

The term "alkenyl" refers to a hydrocarbon group, typically C2 to C4, derived from the corresponding alkyl and which contains at least one double bond (e.g., butadienyl).

The term "alkynyl" refers to a hydrocarbon group, typically C2 to C4, derived from the corresponding alkyl and which contains at least one triple bond (e.g., butadiynyl).

The term "halogen" refers to one of the electronegative elements of group VIIA of the periodic table (fluorine, chlorine, bromine, iodine, astatine).

The term "perfluoroalkyl" refers to an alkyl group where every hydrogen atom is replaced with a fluorine atom.

The term "perfluoroaryl" refers to an aryl group where every hydrogen atom is replaced with a fluorine atom.

The term "pyridyl" refers to an aryl group where one CR unit is replaced with a nitrogen atom.

The term "sulfoxyl" refers to a group of composition RS(O)— where R is some alkyl, aryl, cycloalkyl, perfluoroalkyl, or perfluoroaryl group. Examples include, but are not limited to methylsulfoxyl, phenylsulfoxyl, etc.

The term "sulfonyl" refers to a group of composition $RSO_2$— where R is some alkyl, aryl, cycloalkyl, perfluoroalkyl, or perfluoroaryl group. Examples include, but are not limited to methylsulfonyl, phenylsulfonyl, p-toluenesulfonyl, etc.

The term "carbamoyl" refers to the group of composition $R^1(R^2)NC(O)$-where $R^1$ and $R^2$ are H or some alkyl, aryl, cycloalkyl, perfluoroalkyl, or perfluoroaryl group. Examples include, but are not limited to N-ethylcarbamoyl, NN-dimethylcarbamoyl, etc.

The term "amido" refers to the group of composition $R^1CON(R^2)$— where $R'^1$ and R2 are H or some alkyl, aryl, cycloalkyl, perfluoroalkyl, or perfluoroaryl group. Examples include, but are not limited to acetamido, N-ethylbenzamido, etc.

The term "acyl" refers to an organic acid group in which the —OH of the carboxyl group is replaced by some other substituent (RCO—). Examples include, but are not limited to acetyl, benzoyl, etc.

In preferred embodiments, when a metal is designated by "M" or "M′ⁿ", where n is an integer, it is recognized that the metal may be associated with a counterion.

A linker is a molecule used to couple two different molecules, two subunits of a molecule, or a molecule to a substrate. When all are covalently linked, they form units of a single molecule.

The term "electrically coupled" when used with reference to a light harvesting rod and electrode, or to chromophores, charge separation groups and electrodes, refers to an association between that group or molecule and the coupled group or electrode such that electrons move from the storage medium/molecule to the electrode or from the electrode to the molecule and thereby alter the oxidation state of the storage molecule. Electrical coupling can include direct covalent linkage between the storage medium/molecule and the electrode, indirect covalent coupling (e.g. via a linker), direct or indirect ionic bonding between the storage medium/molecule and the electrode, or other bonding (e.g. hydrophobic bonding). In addition, no actual bonding may be required and the light harvesting rod may simply be contacted with the electrode surface. There also need not necessarily be any contact between the electrode and the light harvesting rod where the electrode is sufficiently close to the light harvesting rod to permit electron tunneling between the medium/molecule and the electrode.

"Excited-state energy" refers to the energy stored in the chromophore in a metastable state following absorption of light (or transfer of energy from an absorber). For an excited singlet (triplet) state, the magnitude of the "excited-state energy" is estimated by energy of the shortest wavelength fluorescence (phosphorescence) band. The magnitude of the "excited-state energy" is greater than or equal to the energy of the separated electron and hole following charge separation.

Electrolytes used to carry out the present invention may be aqueous or non-aqueous electrolytes, including polymer electrolytes. The electrolyte may comprise or consist of a solid, in which latter case the solar cell can be produced devoid of liquid in the space between the first and second substrates. The electrolyte consists of or comprises a substance that increases the electrical conductivity of a carrier medium. Most electrolytes are salts or ionic compounds. Examples include sodium chloride (table salt), lithium iodide, or potassium bromide in water; tetrabutylammonium hexafluorophosphate or tetraethylammoniun perchlorate in acetonitrile or dichloromethane; or an ionic polymer in a gel.

"Mobile charge carriers" refers to an ion, molecule, or other species capable of translating charges (electrons or holes) between the two electrodes in a solar cell. Examples include quinones in water, molten salts, and iodide in a polymer gel such as polyacrylonitrile. Examples of mobile charge carriers include, but are not limited to, iodide, bromide, tetramethyl-1,4-phenylenediamine, tetraphenyl-1, 4-phenylenediamine, p-benzoquinone, $C_{60}$, $C_{70}$, pentacene, tetrathiafulvalene, and methyl viologen.

A. Molecular Design.

Here chlorin building blocks designed to give efficient energy transfer in chlorin-containing light-harvesting arrays are presented. Objectives are to (1) prepare chlorins with two functional handles such that the chlorins can be readily incorporated into linear arrays, (2) design the chlorin building blocks to have the highest possible value of the orientation term for TS energy transfer, and (3) be connected appropriately to give the most extensive TB energy transfer process. Four possible trans-substituted chlorins are displayed in FIG. 2. Two β,β'-substituted chlorins are shown, as are two chlorins each bearing two meso substituents. To evaluate the chlorin building blocks one must consider (1) steric effects of any substituents, (2) the orientation of the transition dipole moment for the long wavelength transition, and (3) the composition of the frontier molecular orbitals.

Figure 2:
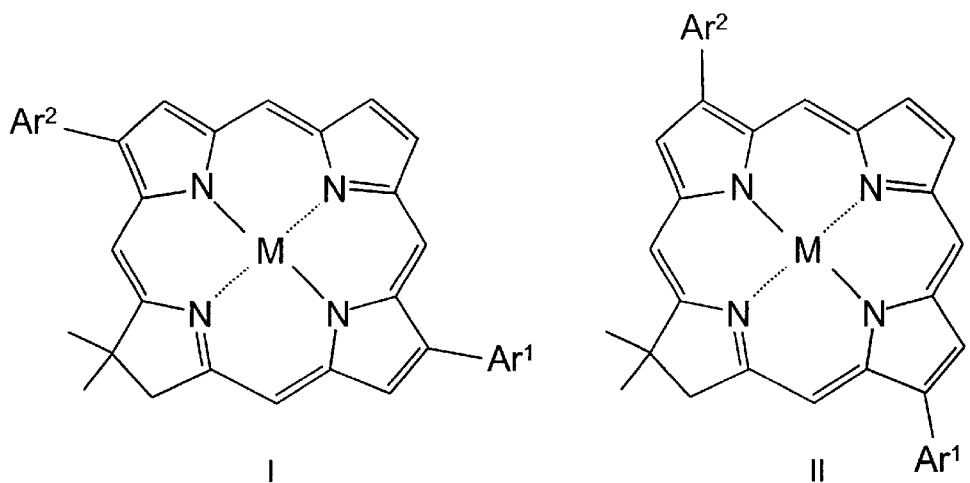
FIG. 2. Four different chlorin building blocks, and chlorin nomenclature showing IUPAC-IUB ring labels A–D.
Figure 2:
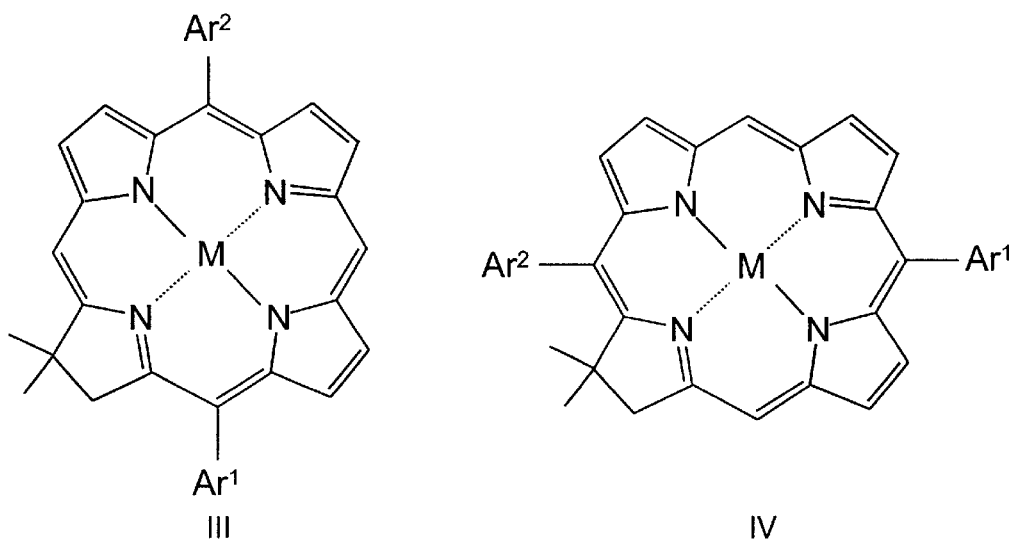
Figure 2:
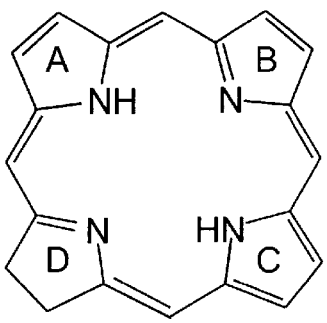

Examination of the four chlorin building blocks in FIG. 2 reveals steric hindrance in chlorin IV due to the interaction of the meso substituent flanking the geminal methyl groups of ring D. The other three chlorins I–III have no such steric interactions and are superior to IV in this regard.

Figure 3:
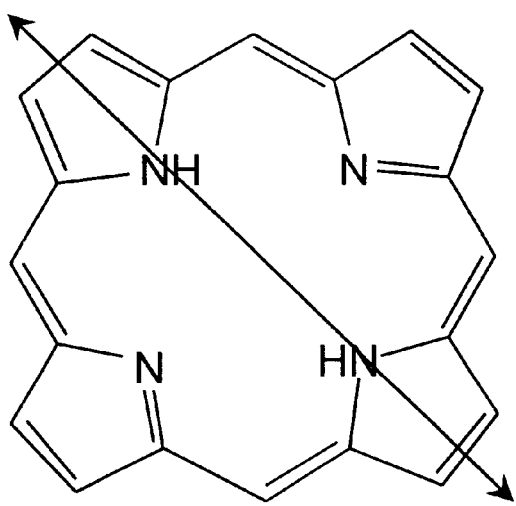
FIG. 3. Orientation of the transition dipole moment of the long-wavelength absorption band in free base chlorin and metallochlorin.
Figure 3:
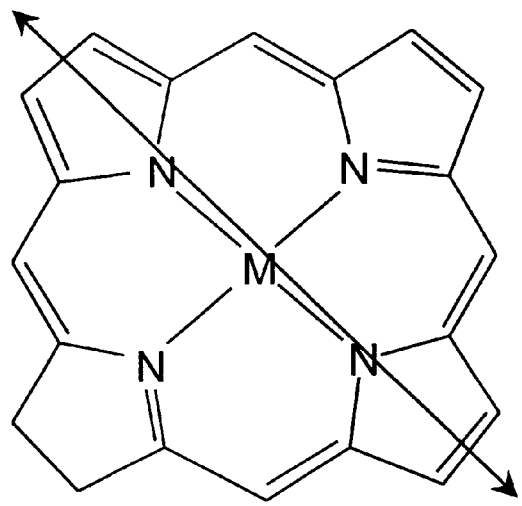
Figure 4:
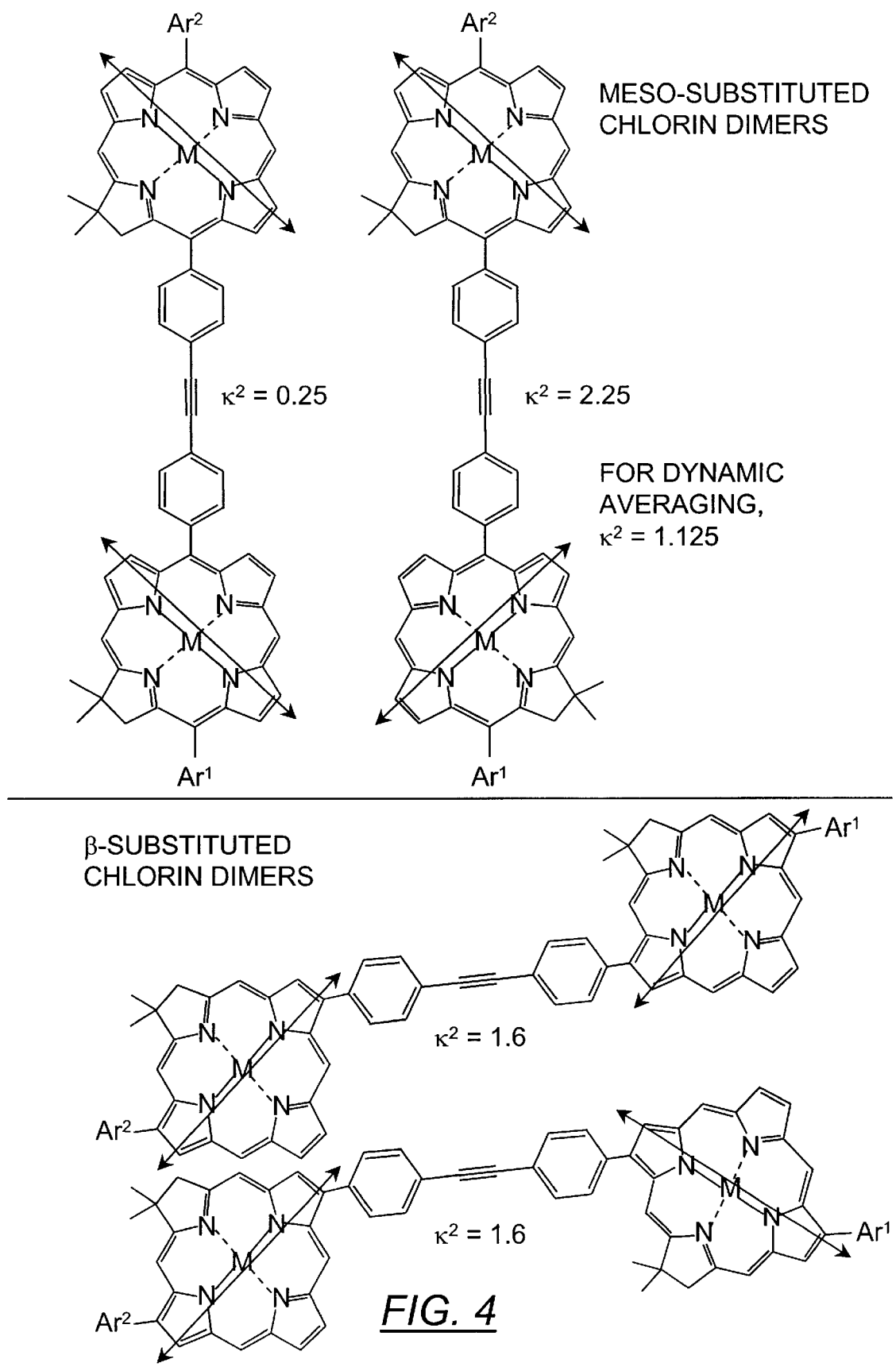
FIG. 4. Pairwise interaction of chlorin building blocks upon incorporation in covalently linked arrays.

The transition dipole moment for the far-red transition in chlorins is polarized along the N—N axis perpendicular to the reduced ring (ring D), transecting rings A and C not rings B and D (FIG. 3). Evaluation of the four possible trans-chlorins shown in FIG. 2 requires consideration of the geometries obtained upon incorporation in covalently linked arrays. The pairwise interactions are displayed in FIG. 4, where a diphenylethyne linker is employed to join the chlorins (other linkers, including a p-phenylene group could also be employed). For the meso-linked chlorins, $\kappa^2$ takes on limiting values of 0.25 and 2.25 depending on orientation. Assuming free rotation during the lifetime of the excited state (dynamical averaging), the average value of $\kappa^2$ is 1.125. Note that free rotation is expected about the cylindrically symmetric ethyne but the rate of rotation may not be sufficient to cause all molecules to explore all conformations during the few ns lifetime of the excited state. Thus, those molecules in an orientation characterized by a zero or near-zero value of $\kappa^2$ will not give rise to efficient TS energy transfer. The β,β-substituted chlorins have limiting $\kappa^2$ values of ~-1.6 and the value remains >1 regardless of dihedral angle about the ethyne linker. (Note that in this case the center-to-center distance changes slightly upon rotation about the ethyne linker.) Thus, the β,β'-substituted chlorins give slightly better collinearity of the transition dipole moment with the axis of substitution (to be the linear axis of the multi-chlorin array) than is obtained with the meso-substituted chlorins. Taken together, chlorin building blocks I and II are slightly preferred over III and IV for TS energy transfer.

Figure 5:
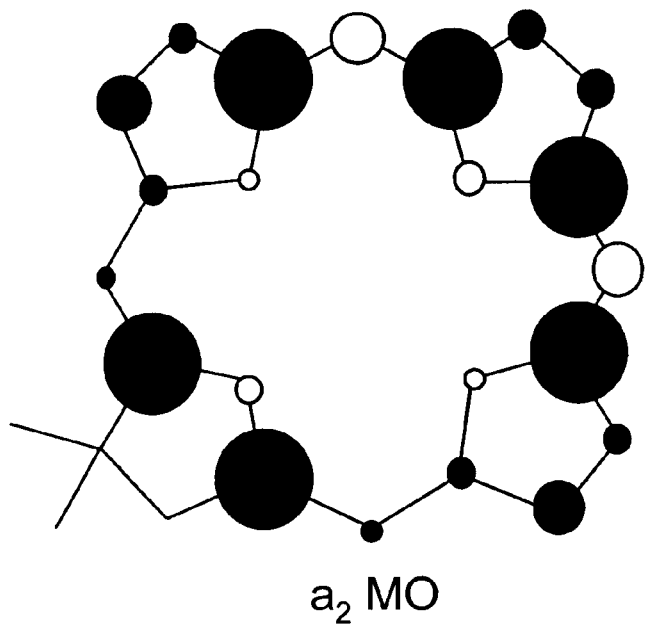
FIG. 5. The highest occupied molecular orbital of a chlorin is an $a_2$ orbital, which places electron density at each of the meso and non-reduced β sites.

The highest occupied molecular orbital of a chlorin is an $a_2$ orbital, which places electron density at each of the meso and β sites (FIG. 5). Accordingly, it is difficult to estimate the relative goodness of meso versus β sites of linker attachment for efficient TB energy transfer. In the absence of this knowledge, the β-substitution chlorins and the meso-substituted chlorins are believed to have comparable utility. In any event, as the distance of separation of the rings becomes quite short, the TS mechanism will dominate and the TB mechanism will become a relatively minor contributor to the observed rate. The chief disadvantage of the meso-substituted trans chlorins stems from possible ruffling of the macrocycle due to steric congestion with the partially saturated ring. The trans configuration can be achieved with connection to rings A and C. Comparing the four possible trans-chlorins shown in Scheme 4 for TB energy transfer, it is seen that the meso-substituted chlorins (III, IV) are inferior to the β,β'-substituted chlorins (I,II).

B. Monomer Synthesis.

Chlorins with substituents in a trans orientation are highly desirable for elaboration into linear light-harvesting rods. Such chlorins include those with substitution at the 2 and 12-positions, the 3 and 13-positions, or the 5 and 15-positions. We have developed routes to chlorin building blocks bearing substituents at the 2 and 12-positions. The starting material for the synthesis of 2,12-substituted chlorins is a 2-formyl-3-aryl pyrrole. The synthesis of the latter involves formylation of a 3-aryl pyrrole. In this formylation reaction, a mixture of products is produced consisting of the desired 2-formyl-3-aryl pyrrole (major product) and a 5-formyl-3-aryl pyrrole (minor product). The latter is formally, but more confusingly, named as the 2-formyl-4-aryl pyrrole. The two products are separated by fractional crystallization. The 2-formyl-4-aryl pyrrole provides the key starting material for preparation of the 3,13-substituted chlorins. The synthesis of the Western half and Eastern half proceed in the same manner as for the 2,12-substituted compounds. The overall routes are outlined in the following scheme.

Route to a 2,12-Disubstituted Chlorin Building Block

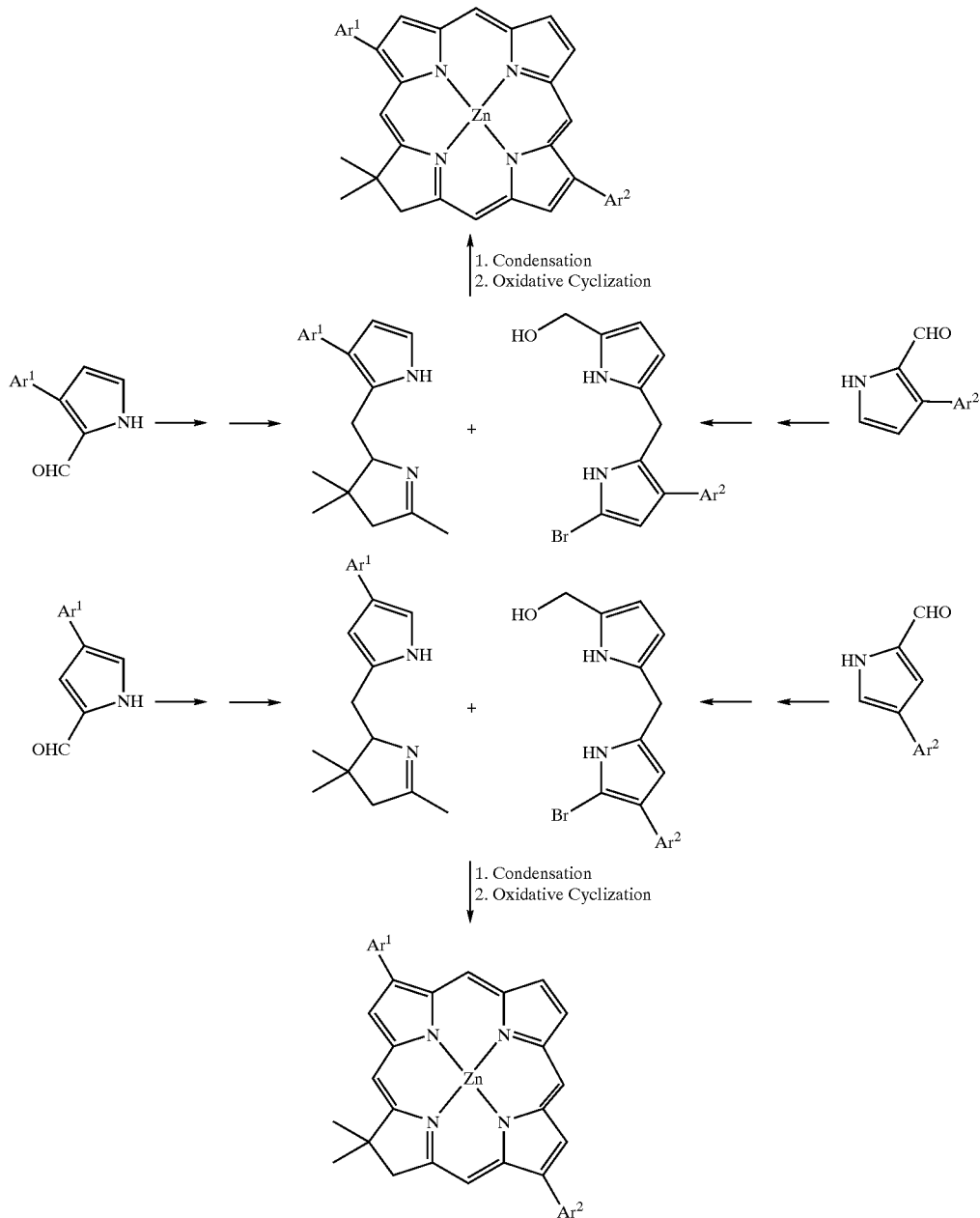

Route to a 3,13-Disubstituted Chlorin Building Block

In overview, a trans-substituted chlorin of the present invention comprises compounds of Formula X:

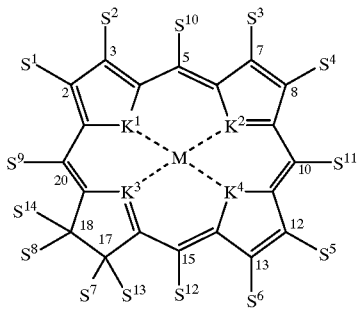

(X)

wherein:

M is a metal, such as a metal selected from the group consisting of Zn, Mg, Pt, Pd, Sn and Al, or M is absent (in which case the ring hetero atoms $K^1$ through $K^4$ are substituted with H,H as required to satisfy neutral valency);

$K^1$, $K^2$, $K^3$, and $K^4$, are hetero atoms, such as hetero atoms independently selected from the group consisting of N, O, S, Se, Te, and CH. Preferably, K is N.

$S^1$, $S^2$ $S^3$, $S^4$, $S^5$, $S^6$, $S^7$, $S^8$, $S^9$, $S^{10}$, $S^{11}$, $S^{12}$, $S^{13}$, and $S^{14}$ are independently selected substituents (that may optionally provide a redox potential of less than about 5, 2 or even 1 volt). Example substituents include, but are not limited to, H, aryl, phenyl, cycloalkyl, alkyl, alkenyl, alkynyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl;

optionally but preferably, one, two three or four of $S^1$ through $S^{14}$ are linking groups Q; and more preferably either $S^1$ and $S^5$ are the trans-substituted linking groups $Q^1$ and $Q^2$, or $S^2$ and $S^6$ are trans-substituted linking groups $Q^1$ and $Q^2$; and $S^7$ and $S^{13}$ together may optionally form=O (an oxochlorin).

Preferably, when $S^7$ and $S^{13}$ are an oxo group=O, then neither $S^8$ nor $S^{14}$ are H. Preferably, when $S^7$ and $S^{13}$ are not an oxo group, then not more than two of $S^7$, $S^8$, $S^{13}$, and $S^{14}$ are H, and then only when the both H groups are bound to the same carbon.

Note numbering in Formula X departs from the current IUPAC scheme to make clear the correct tautomer. The trans-substituted linking groups $Q^1$ and $Q^2$ are independently selected linking groups of the formula:

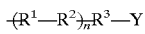

wherein:

5 n is from 0 or 1 to 5 or 10;

$R^3$ may be present or absent (in one embodiment when n is 0 then $R^3$ is present; in another embodiment, when n is 0 $R^3$ may also be absent);

$R^1$, $R^2$, and $R^3$ are each independently selected from the group consisting of ethene, ethyne, aryl, and heteroaryl groups (e.g., phenyl, and derivatives of pyridine, thiophene, pyrrole, phenyl, etc.), which aryl and heteroaryl groups may be unsubstituted or substituted one or more times with H, aryl, phenyl, cycloalkyl, alkyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl.

Y may be a protected or unprotected reactive site or group on the linker such as a hydroxy, thio, seleno, telluro, carboxy, ester, carboxylic acid, boronic acid, phenol, silane, sulfonic acid, phosphonic acid, alkylthiol, formyl, halo (e.g., iodo, bromo, chloro), alkenyl, alkynyl, haloalkyl, haloalkyl, alkyl phosphonate, alkyl sulfonate, alkyl carboxylate, and alkyl boronate groups.

In general, trans-substituted chlorins as described above are made by:

(a) condensing a compound of formula WH with a compound of formula EH in an organic solvent in the presence of an acid to form a condensation product;

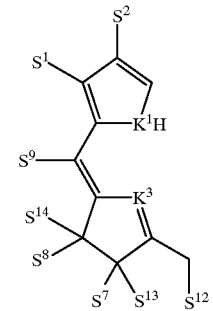

WH

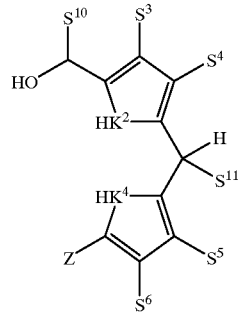

EH wherein Z is halo (e.g., Br, Cl, I), alkoxy, or acetoxy; and then (b) oxidatively cyclizing said condensation product in an organic solvent in the presence of a base, an oxidant and a metal salt $MX_t$, where X is an anion and t is 2–3, to produce a compound of Formula X above; and then (c) optionally removing metal M by displacement with an acid to create a free base chlorin.

The condensing step is carried out under acidic conditions (e.g., 1 or 10 to 20 or 200 mM, depending upon the acid) in an organic solvent. The organic solvent is typically a polar or nonpolar, protic or aprotic solvent such as methylene chloride, acetonitrile, or toluene. A Bronsted or Lewis acid is included in the solvent, such as trifluoroacetic acid or $BF_3$-etherate. The condensing step may be carried out at any suitable temperature and pressure, such as 0° to 25° C. and ambient pressure.

The oxidative cyclization step is carried out in a polor or nonpolar, protic or aprotic organic solvent as described above, in the presence of a metal salt $MX_2$ or $MX_3$, where X is an anion such as acetate, chloride, iodide, etc. Any suitable base may be employed, with piperidine currently preferred. Any suitable oxidant may be employed, with silver iodate or oxygen currently preferred. The reaction may be carried out at any suitable temperature and pressure, such as 25° to 100° C. and ambient pressure.

After formation of the chlorin, metal M may optionally be removed to form the free base chlorin simply by displacing with an acid (e.g., acetic acid, trifluoroacetic acid, hydrochloric acid, sulfuric acid, etc.) in accordance with standard techniques.

As explained in greater detail below, the synthesis of the β-substituted chlorin building blocks follows in part the general route previously established for preparing meso-substituted chlorins. In this route, an Eastern half and a Western half undergo condensation followed by oxidative cyclization to give the chlorin. The same approach is used here with a new Eastern half and a new Western half, each bearing one β substituent (FIG. 6).

Figure 7A:
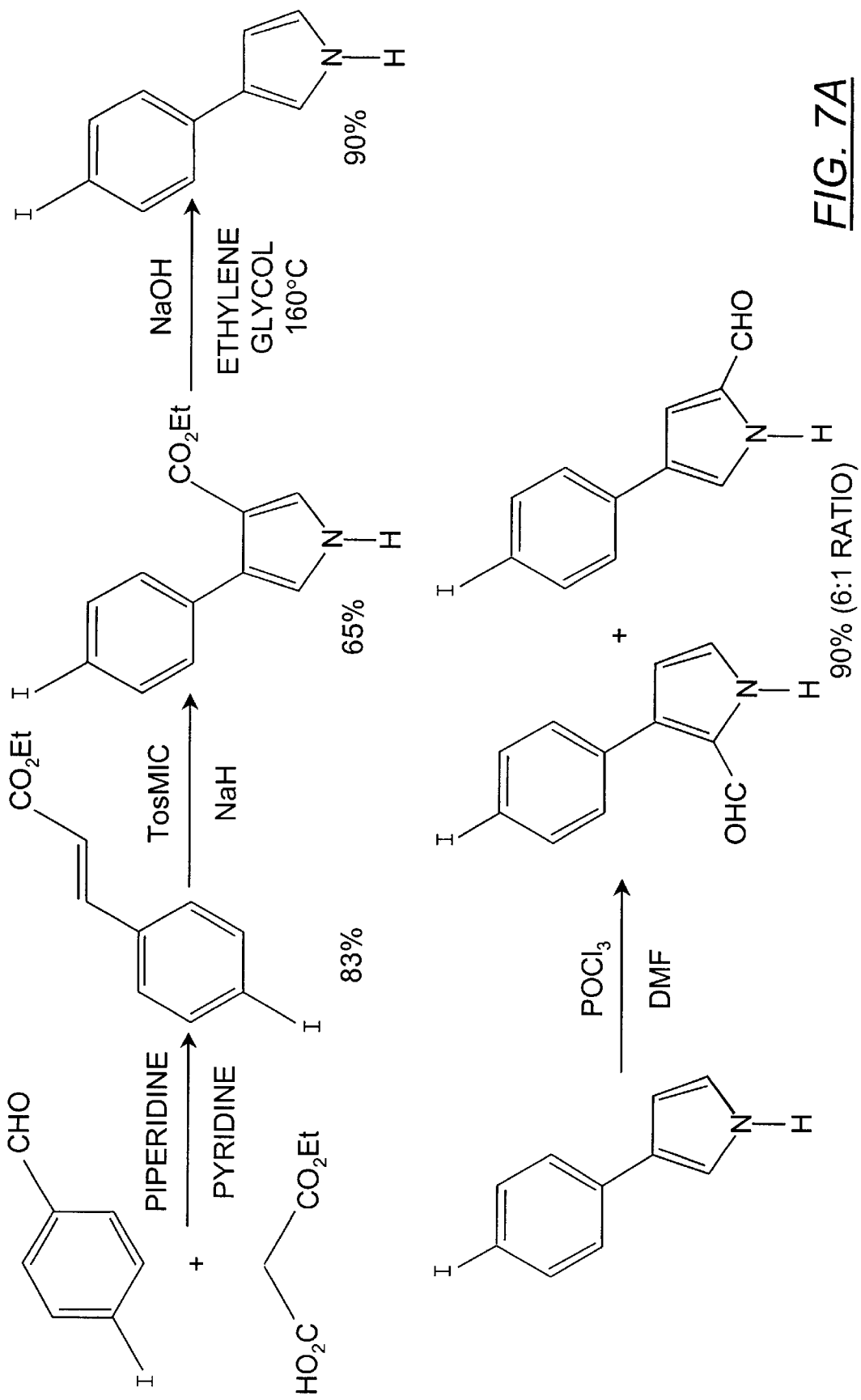
FIG. 7A. The synthesis of the new β-substituted Eastern half for chlorin synthesis.
Figure 7B:
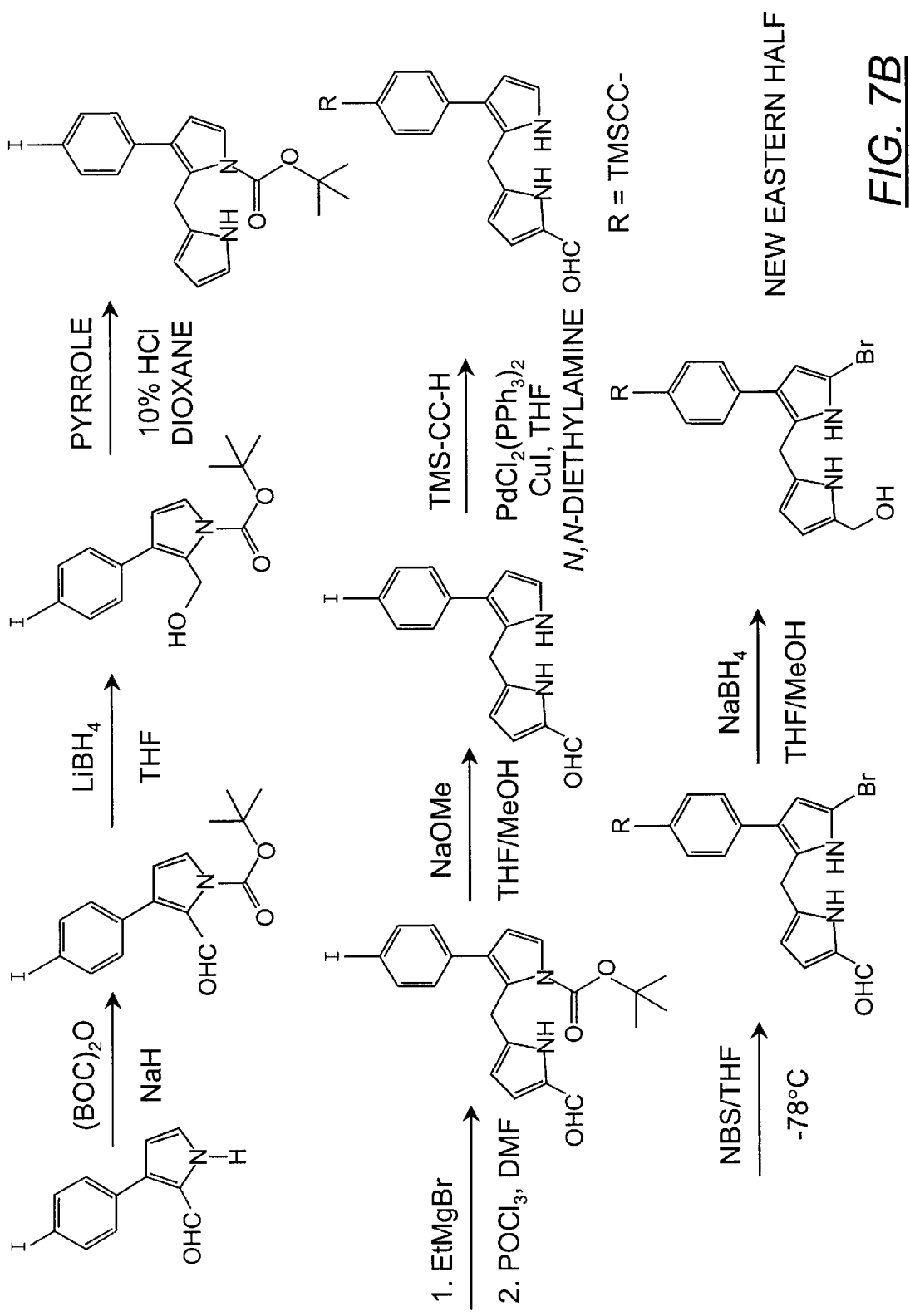
FIG. 7B. The synthesis of the new β-substituted Eastern half for chlorin synthesis, extending the route shown in FIG. 34A.

The synthesis of the new β-substituted Eastern half is shown in FIGS. 7A and 7B. This synthesis, which builds on prior work in developing a route to β-substituted porphyrin building blocks (Balasubramanian, T.; Lindsey, J. S. *Tetrahedron* 1999, 55, 6771–6784), is described in the examples below.

Figure 8:
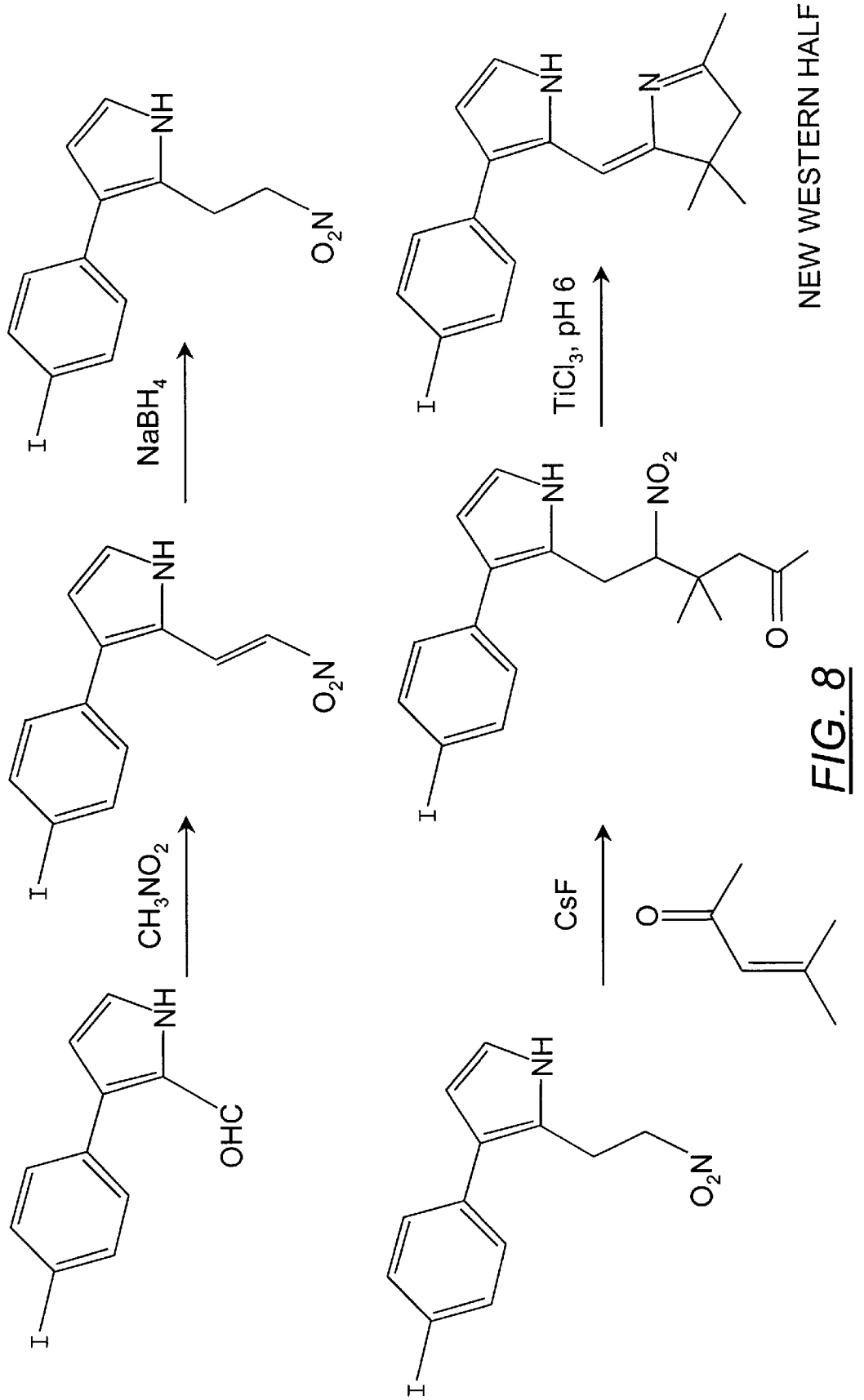
FIG. 8 illustrates the synthesis of the new β-substituted Western half for a chlorin building block.

The synthesis of the new β-substituted Western half is shown in FIG. 8. This route begins with the same critical intermediate as used in the Eastern half, a 2-formyl-3-arylpyrrole (FIG. 7A). The Western half is then prepared following the same sequence of reactions employed for the unsubstituted Western half.

Figure 6:
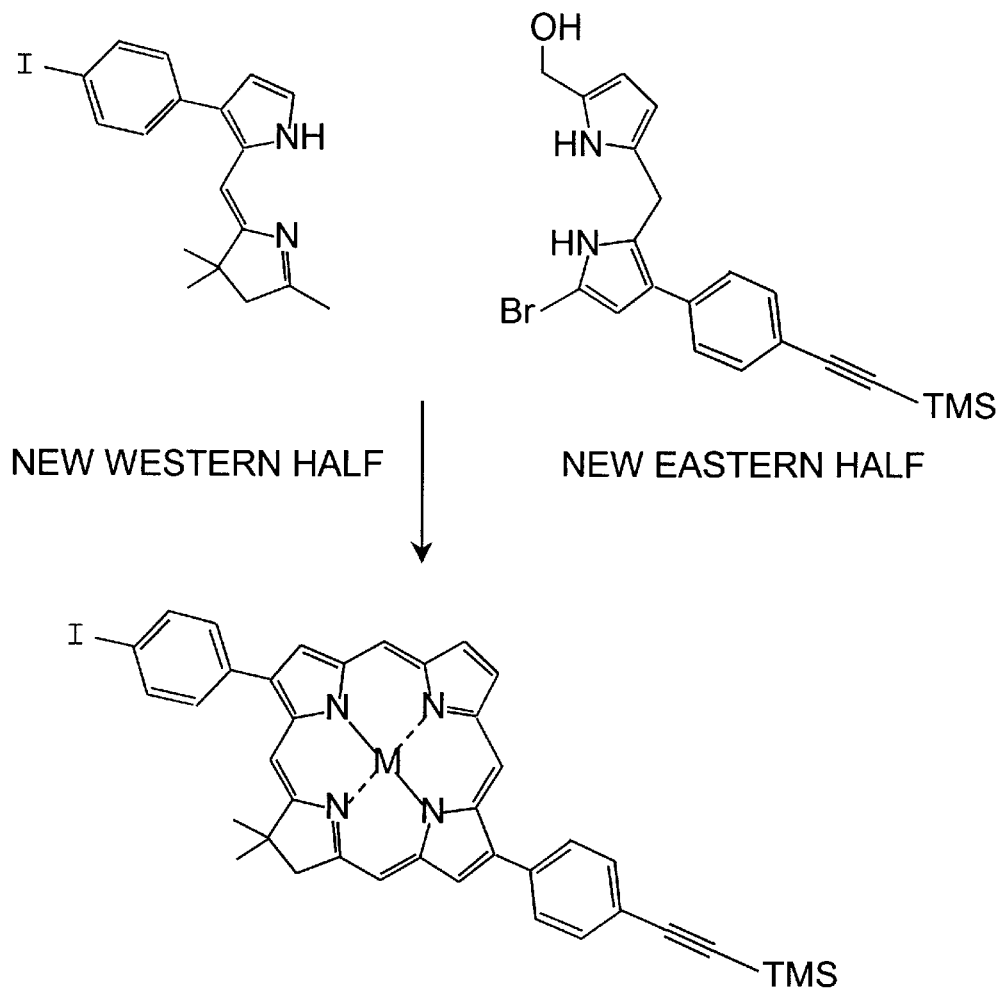
FIG. 6 illustrates the synthesis of a trans-chlorin building block with two β substituents.
Figure 9:
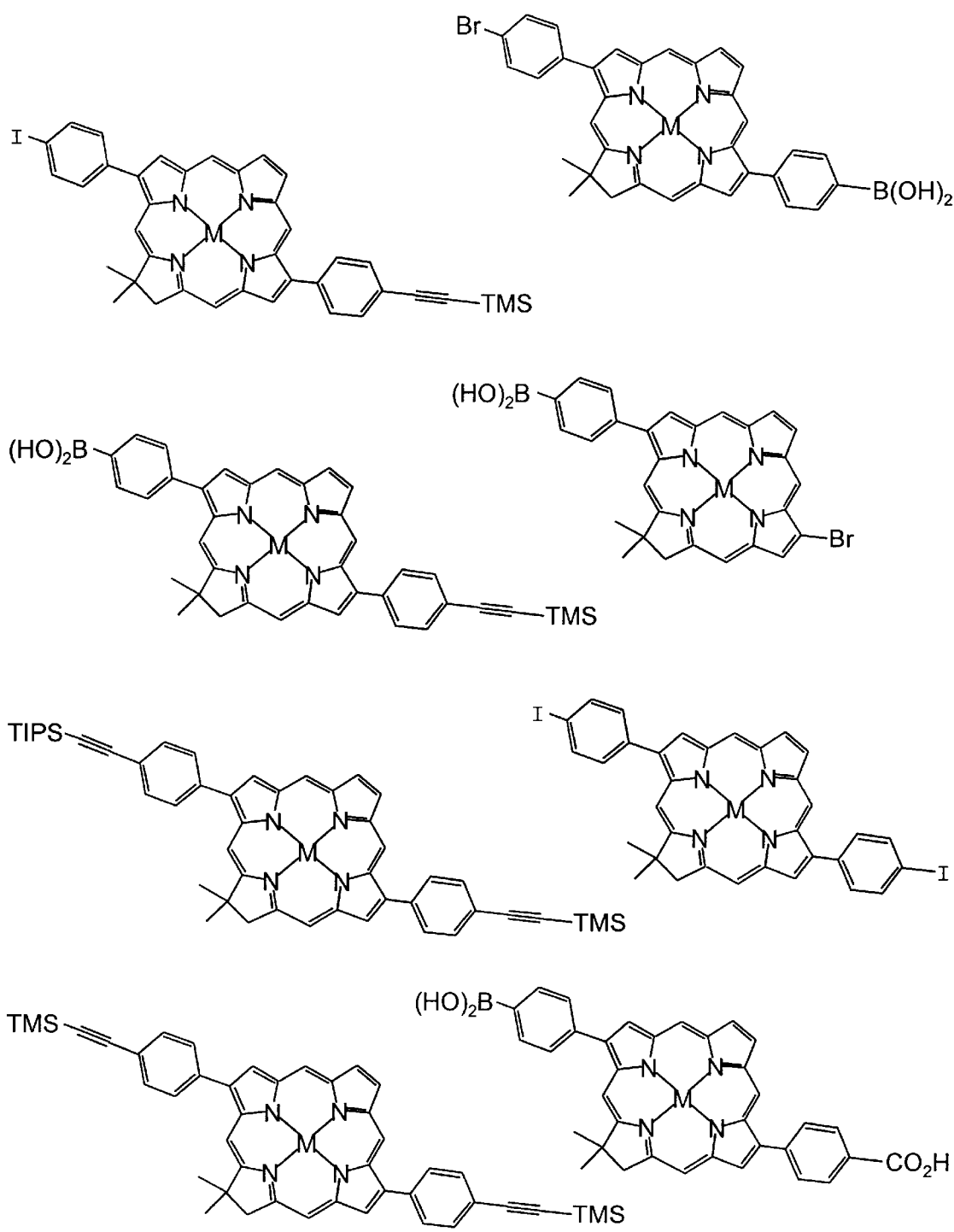
FIG. 9. Other chlorin building blocks that are accessible via this same synthetic strategy shown above, and that have substantially the same physical properties.

The chlorin building block shown in FIG. 6 bears one 4-(TMS-ethynyl) phenyl group and one 4-iodophenyl group. This particular building block should enable the synthesis of diphenylethyne linked chlorin containing arrays in a linear architecture. Other chlorin building blocks that are accessible via this same synthetic strategy, and that have the same desirable physical properties, are shown in FIG. 9.

For all of the chlorin building blocks, a wide variety of metals can be employed, given that the metals meet the requirement of affording a photochemically active excited state. Preferred embodiments of such metals are Zn, Mg, Pd, Sn, and Al. The free base chlorin (M=H, H) can also be employed. In the syntheses employed, the chlorin-forming reaction yields the zinc chlorin, which is easily demetalated with mild acid to give the free base chlorin. The desired metallochlorin can then be prepared via well known metalation reactions.

Figure 10:
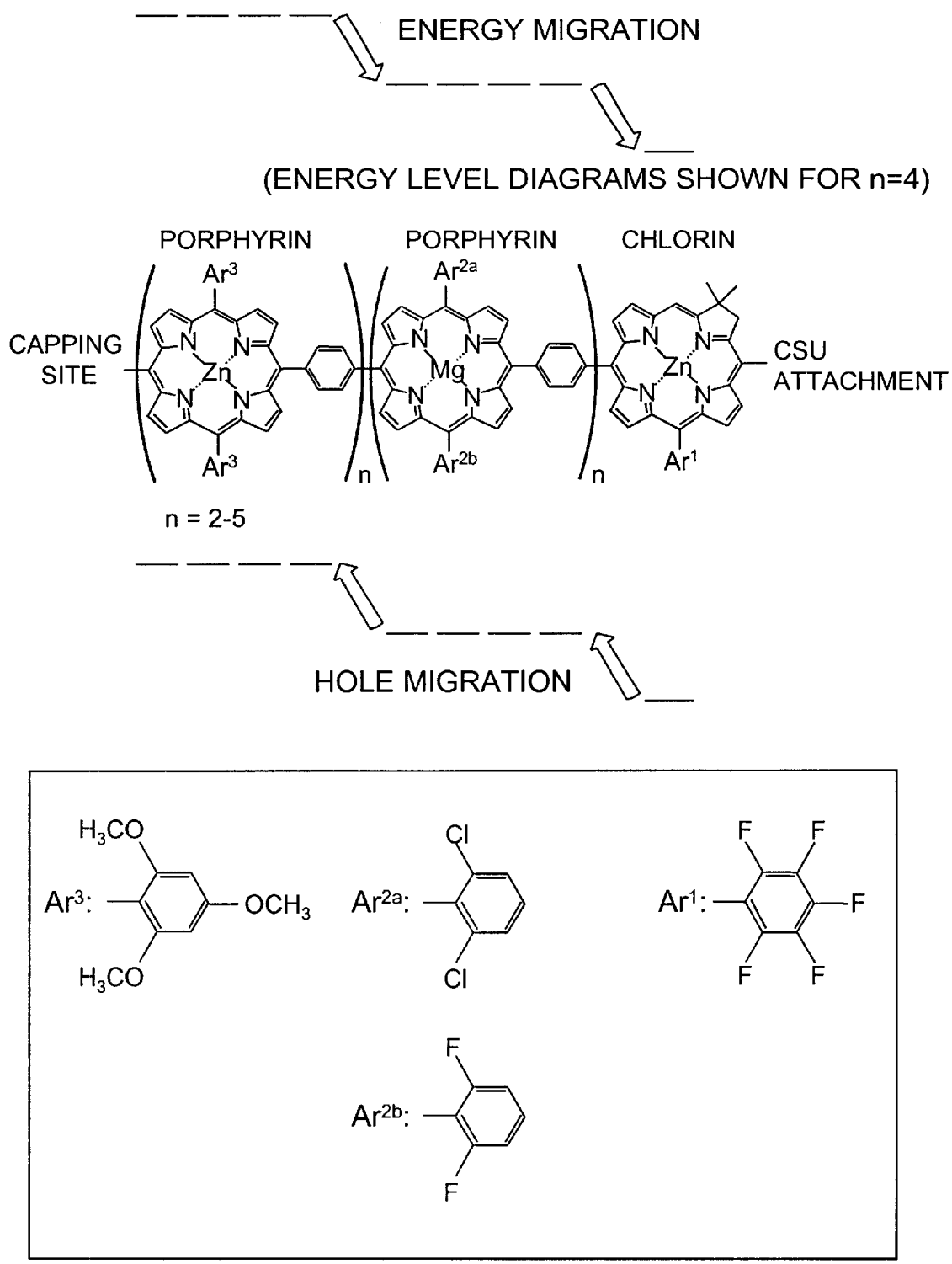
FIG. 10 illustrates a cataract linear array employing domains comprised of multiple isoenergetic pigments.

Just one example of a light harvesting array, this array employing multiple isoenergetic pigments (one or more of which may be chlorins of the present invention), is illustrated in FIG. 10. Such arrays may be produced in accordance with known techniques and the techniques disclosed below.

C. Synthesis of Oxochlorins.

Oxochlorins may be considered as a particular type of chlorin. Oxochlorins and chlorins have similar spectral properties but the oxochlorins are more resistant to oxidation than are chlorins. In fact, oxochlorins have oxidation potentials similar to those of porphyrins whereas chlorins have lower oxidation potentials than porphyrins. Thus, broadly speaking, an oxochlorin has the spectral properties of a chlorin and the oxidation properties of a porphyrin.

The time-honored method for forming oxochlorins employs treatment of a substituted porphyrin with $OsO_4$ forming the vicinal diol, which upon acid-catalyzed pinacol rearrangement yields the oxochlorin bearing a geminal dialkyl group (Chang, C. K.; Sotiriou, C. *J. Heterocyclic Chem.* 1985, 22:1739–1741). However, application of this approach to porphyrin building blocks bearing specific patterns of substituents at the perimeter of the macrocycle typically results in a mixture of oxochlorins (Osuka, A., et al., *J. Am. Chem. Soc.* 1996, 118:155–168). Battersby found that the attempted synthesis of a chlorin by reaction of an Eastern half and a Western half in the presence of copper acetate in air afforded the oxochlorin directly (Battersby, A. R., et al., *J. Chem. Soc. Perkin Trans.* 1 1984, 2725–2732). He stated in his paper that spectral monitoring indicated the chlorin was forming first and then undergoing oxidation to give the oxochlorin. The same reaction in the absence of air afforded the chlorin. While the oxochlorin was an undesired byproduct in Battersby's synthesis, the oxochlorin incorporated the keto functionality at a specific site and did not occur as a mixture of isomers.

In our synthesis, we employ zinc acetate in air to form the chlorin upon reaction of an Eastern half and a Western half. The chlorin so obtained can be oxidized to the oxochlorin, introducing the keto functionality adjacent to the geminal dimethyl group by oxidation of the isolated methylene group. Oxidation can be achieved by a variety of methods, including treatment with copper acetate and air, or oxidation with a number of reagents known to oxidize isolated methylene units. Such reagents include $SeO_2$, $MnO_2$, and $CrO_3$.

D. Polymer Synthesis.

In general, a polymer of the present invention comprises a plurality of monomers, each of said monomers comprising a porphyrinic macrocycle, wherein at least one (e.g., two, three or all) of said porphyrinic macrocycles is an independently selected chlorin, and wherein each of said chlorins is: (i) coupled to one or two adjacent porphyrinic macrocycles in said polymer at the 2 position, the 12 position, or both the 2 and 12 positions (when the monomer is internal); or (ii) coupled to one or two adjacent porphyrinic macrocycles in said polymer at the 3 position, the 13 position, or both the 3 and 13 positions (when the monomer is internal). The monomers in the polymer may be directly linked to one another via a covalent bond or linked via linking groups, depending upon the monomer used and the synthetic reaction employed. The polymer may be of any size, but typically consists of from 2 or 3 to 50, 100 or 200 porphyrinic macrocycle monomers. The polymer may be bound to a conductive substrate to form an electrode, which electrode may be used in the light harvesting arrays and solar cells described herein.

The synthesis of oligomers of porphyrinic macrocycle building blocks (BB), or light-harvesting rods, can proceed via several different types of reactions. A general issue is that the reaction used to join the pigment building blocks into a dyad architecture also creates the linker that provides electronic communication between the two pigments. Accordingly, a more limited set of reactions is generally envisaged than that in the entire corpus of organic chemistry. The methods for synthesis of polymeric arrays of porphyrinic macrocycle building blocks include but are not restricted to use of the following types of reactions (FIG. 11):

Glaser (or Eglinton) coupling of a monomeric pigment building blocks (generating a butadiyne linker)

Cadiot-Chodkiewicz coupling of two different pigment building blocks (generating a butadiyne linker joining a block copolymer)

Sonogashira coupling of two different pigment building blocks (generating an ethyne linker joining a block copolymer)

Heck or Wittig reactions of two different pigment building blocks (generating an alkene linker joining a block copolymer)

Suzuki coupling of two different pigment building blocks (generating a phenylene or biphenyl linker joining a block copolymer)

Polymerization of pigment building blocks bearing substituents such as two or more thiophene groups (generating an oligothiophene linker) or two or more pyrrole groups (generating a polypyrrole linker).

The synthesis of the oligomers can be performed using stepwise methods or using polymerization methods. Both methods generally require two reactive groups attached to the pigment building block in order to prepare a polymer where the pigment building blocks are integral components of the polymer backbone. (An alternative, less attractive design yields pendant polymers where the pigment building blocks are attached via one linkage to the polymer backbone.) The stepwise synthetic method generally requires the use of protecting groups to mask one reactive site, and one cycle of reactions then involves coupling followed by deprotection. In the polymerization method no protecting groups are employed and the polymer is prepared in a one-flask process.

The polymerizations can take place in solution or can be performed with the polymer growing from a surface. The polymerization can be performed beginning with a solid support as in solid-phase peptide or DNA synthesis, then removed, purified, and elaborated further for specific applications. The polymerization with the nascent polymer attached to an electroactive surface generates the desired light-harvesting material in situ. This latter approach is exceptionally attractive in eliminating the need for handling of the polymers. The ability to avoid handling of the polymers makes possible the synthesis of compounds that do not exhibit sufficient solubility in most solvents for convenient handling (dissolution, purification, processing, solution characterization).

Polymers can be created that are composed of identical units, or dissimilar units as in block copolymers or random copolymers. Alternatively, the polymerization can be performed to create a linear array where the composition of different pigment building blocks is organized in a gradient. This latter approach affords the possibility of creating an energy cascade for the flow of excited-state energy and/or the reverse flow of ground-state holes in a systematic manner along the length of the array.

The following describes the in situ synthesis of the cascade polymers on an electroactive surface such as gold or $TiO_2$: A polymerizable unit (pigment building block or linker) is attached to the surface (for Au, a thiol attachment group is used for $Y^1$; for $TiO_2$, a carboxylic acid attachment group is used for $Y^2$). The first pigment building block ($BB^1$) is added and the coupling reagents are added in order to perform the polymerization (e.g., a Glaser coupling). Then the surface is washed to remove the coupling reagents (copper reagents in the case of the Glaser coupling) and any unreacted $BB^1$. Then the second pigment building block ($BB^2$) is added followed by coupling reagents and the polymerization is allowed to continue. The same wash procedure is performed again and then the third pigment building block ($BB^3$) is added followed by coupling reagents and the polymerization is allowed to continue. Repetition of this process enables the systematic construction of a linear array of pigment building blocks with graded energy levels for the flow of excited-state energy and ground-state holes. The last monomer attached bears a single reactive site (J-L-(BB)-L-Y) and the attachment group Y is used for subsequent coupling to an opposing surface. Characterization of the surface-immobilized polymer is achieved by absorption spectroscopy, IR spectroscopy, reflectance spectroscopy and laser desorption time of flight mass spectrometry.

Figure 12:
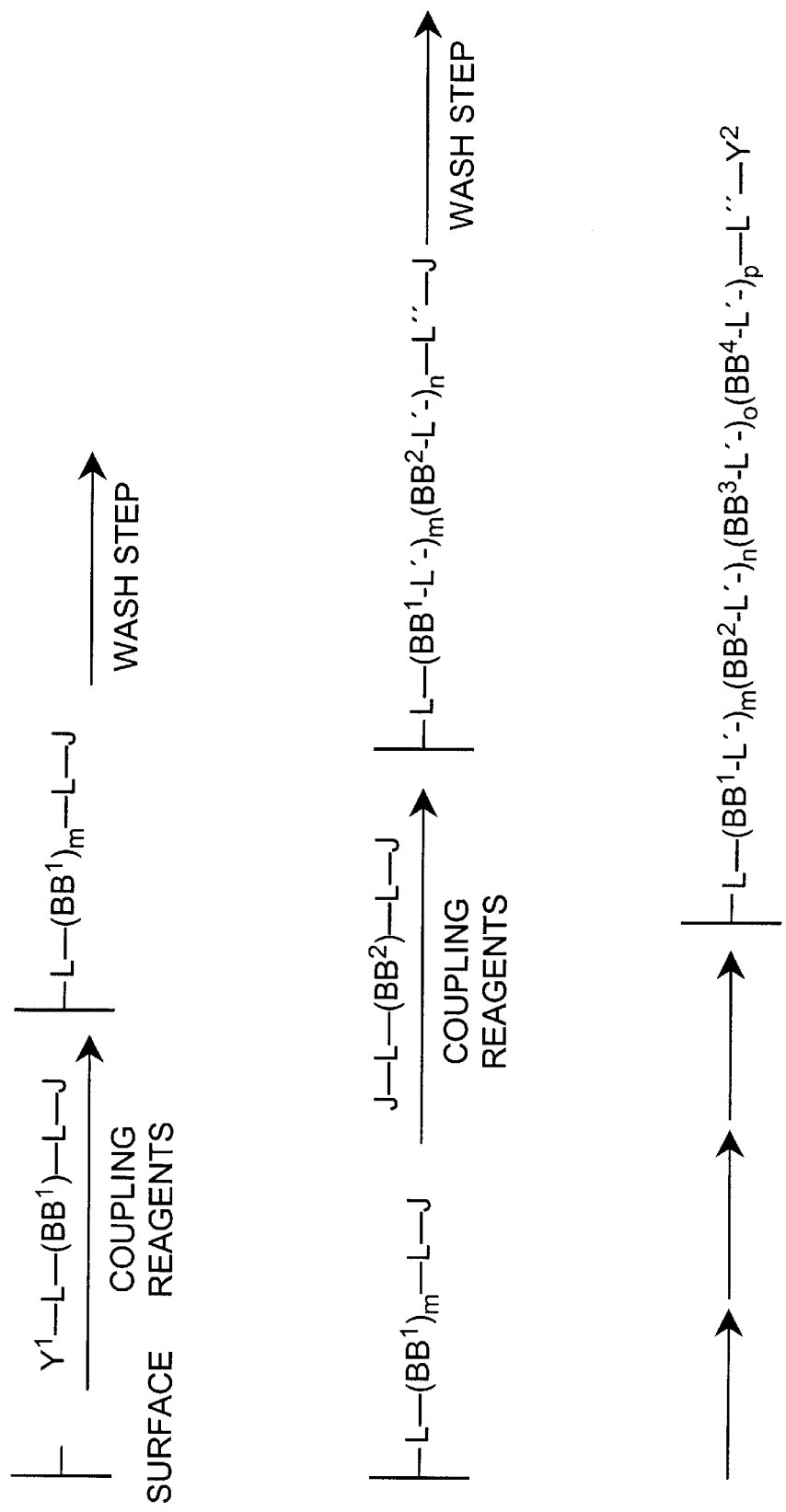
FIG. 12. In situ polymerization yielding a light-harvesting rod on a surface (e.g., Au or $TiO_2$) that will serve as one of the solar cell electrodes.

In the example shown (see FIG. 12), for a surface of Au, a thiol attachment group (X) is used, creating the self-assembled monolayer on gold. Such self-assembled monolayers are known for thiol-derivatized porphyrins (Gryko, D. T. et al., *J. Org. Chem.* 1999, 64, 8635–8647). For the other surface composed of $TiO_2$, a carboxylic acid attachment group is used for the attachment (Y). The polymerizable groups can be any of the type described above using the various name reactions (Glaser, Sonogashira, Cadiot-Chodkiewicz, Heck, Wittig, Suzuki, etc.). The final polymeric product is comprised of domains of the various pigment building blocks $[(BB^1)_n]$ in a linear array.

Chlorin monomers and chlorin-containing polymers of the present invention are useful for the production of light harvesting arrays and solar cells as described above, and as active agents for photodynamic therapy. Solar cells of the present invention can be used in a variety of different electrical devices. Such devices typically comprise a solar cell as described above, and a circuit (e.g., a resistive load) electrically coupled to said solar cell (e.g., by providing a first electrical coupling of the circuit to one electrode of the solar cell, and a second electrical coupling of the circuit to the other electrode of the solar cell). The solar cell may provide the sole source of power to the circuit, may be a supplemental source, may be incorporated to charge a battery, etc. Any of a variety of different electrical devices may incorporate a solar cell of the invention, including but not limited to radios, televisions, computers (such as personal computers), processors, calculators, telephones, wireless communication devices such as pagers, watches, emergency location devices, electric vehicles, emergency power supplies, power generators, lights or lamps, and other illuminating devices, monitoring devices, inspection devices, radiation detectors, imaging devices, optical coupling devices.

The following examples are provided to illustrate certain aspects of the invention, and are not to be construed as limiting thereof.

EXAMPLES

Rational Synthesis of β-Substituted Chlorin Building Blocks

Figure 13:
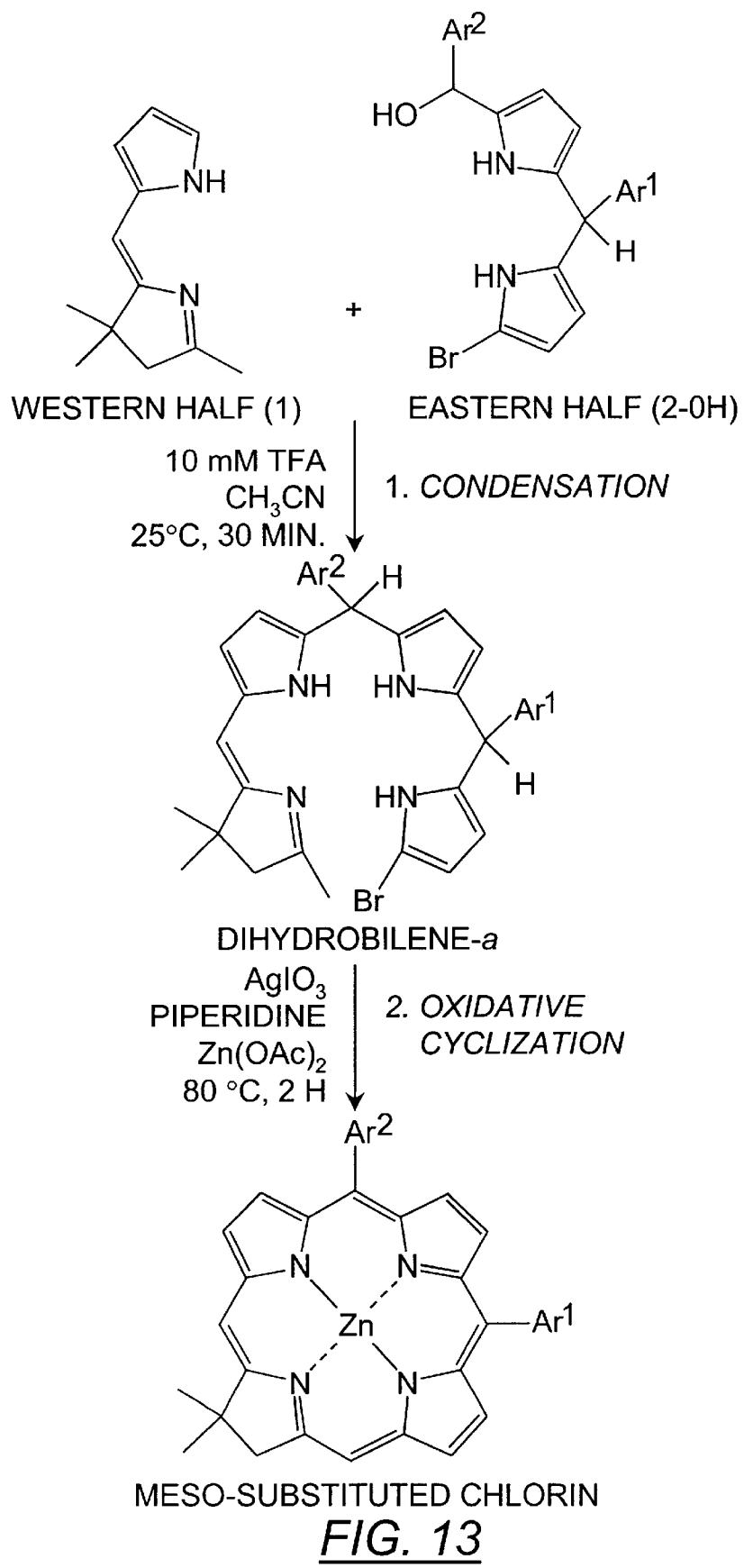
FIG. 13 illustrates the synthesis of meso-substituted chlorins by previously disclosed techniques.

In these examples the synthesis of β-substituted chlorin building blocks is presented. Two new Eastern halves have been constructed in which each bears one β substituent and one (non-flanking) meso substituent, and one new Western half has been prepared that bears one β substituent. These new precursors have been used in conjunction with the prior Western half (1) to yield three new chlorins each bearing one β and one meso substituent. A chlorin bearing one meso substituent and substituents at the 2 and 12 positions also has been prepared. Such building blocks have heretofore not been available and in conjunction with the meso-substituted chlorins previously disclosed (synthesis summarized in FIG. 13), should enable a variety of fundamental studies, including investigation of the effects of site of linker connection on electronic communication in various chlorin-based architectures.

Results and Discussion

Synthesis of the Eastern Half (EH):

The synthesis of the β-substituted EH begins in the same manner as the prior synthesis of β-substituted dipyrromethanes (Balasubramanian, T.; Lindsey, J. S. *Tetrahe-*

Figure 14:
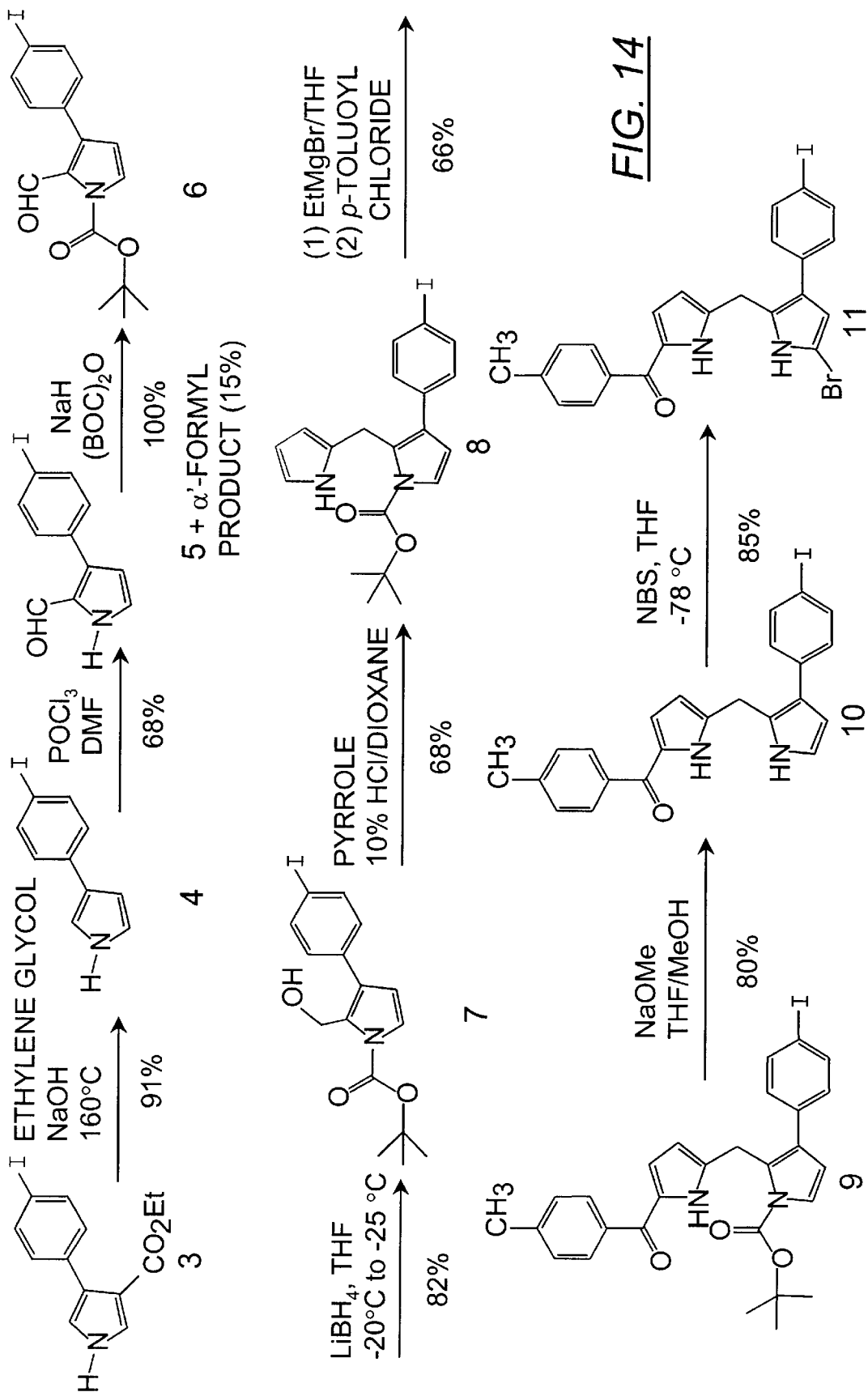
FIG. 14 illustrates the synthesis of β-substituted chlorin eastern half (EH) precursors.

*dron* 1999, 55, 6771–6784) but employs a number of significant improvements (FIG. 14). The iodophenyl substituted pyrrole (3) is readily prepared from 4-iodobenzaldehyde, monoethyl malonate, and tosylmethylisocyanide. The ethoxycarbonyl group was removed by treatment with NaOH in ethylene glycol at 160° C. to give the 3-(4-iodophenyl)pyrrole (4) in 91% yield as pale brown crystals. It is noteworthy that this single-step decarboxylation is superior to the two-step transformation on similar pyrrole compounds (Pavri, N. R.; Trudell, M. L. *J. Org. Chem.* 1997, 62, 2649–2651). Vilsmeier-Haack formylation of 4 yielded a mixture of two regioisomers (~6:1 ratio) which were readily distinguished by $^1$H NMR spectroscopy (See Experimental Section). The major isomer was the desired compound (5) and was obtained in pure form by recrystallization in 62% yield. Protection of the pyrrolic nitrogen with the BOC group (Tietze, L. F.; Kettschau, G.; Heitmann, K. *Synthesis* 1996, 851–857) gave pyrrole 6 in quantitative yield. Reduction to alcohol 7 was achieved by treatment with LiBH$_4$ at low temperature (longer reaction time or higher temperature led to the over-reduced and deprotected compound 2-methyl-3-(4-iodophenyl)pyrrole). Treatment of 7 with excess pyrrole under acidic conditions furnished the β-substituted, mono-protected dipyrromethane 8 in 68% yield. Excess pyrrole is necessary to minimize the formation of the tripyrromethane, while protection of the pyrrolic nitrogen is necessary to facilitate the reaction, avoid self condensation and allow the subsequent selective monoacylation. This methodology afforded the β-substituted dipyrromethane as a single regioisomer, in contrast to earlier methodology which gave a mixture of two regioisomers (Balasubramanian, T.; Lindsey, J. S. *Tetrahedron* 1999, 55, 6771–6784).

Methods for acylation of 5-substituted dipyrromethanes have been developed that involve formation of the pyrrolic Grignard reagent followed by treatment with an acid chloride (Lee, C.-H.; Li, F.; Iwamoto, K.; Dadok, J.; Bothner-By, A. A.; Lindsey, J. S. *Tetrahedron* 1995, 51, 11645–11672). In this case, the N-protected dipyrromethane was retained for selective monoacylation of the α-position in the unprotected pyrrole unit. Treatment of 8 with 2.5 equivalents of EtMgBr in THF followed by p-toluoyl chloride afforded the monoacylated dipyrromethane 9 in 66% yield (FIG. 14). However, similar reaction in toluene led to a mixture of the mono-acylated product, deprotected compound and some unidentified impurities. A control experiment involving treatment of 8 with a slight excess of EtMgBr at 0° C. in THF for 1 h and the usual workup afforded the starting material in quantitative yield, thus revealing that the BOC group is stable to the acylation conditions. Removal of the BOC group under standard conditions (Hasan, I. et al., *J. Org. Chem.* 1981, 46, 157–164) gave 10. Electrophilic bromination of 10 with NBS (1 equiv) in THF at –78° C. following earlier methods (excess NBS led to a considerable amount of a dibromo compound) afforded 11.

Figure 15:
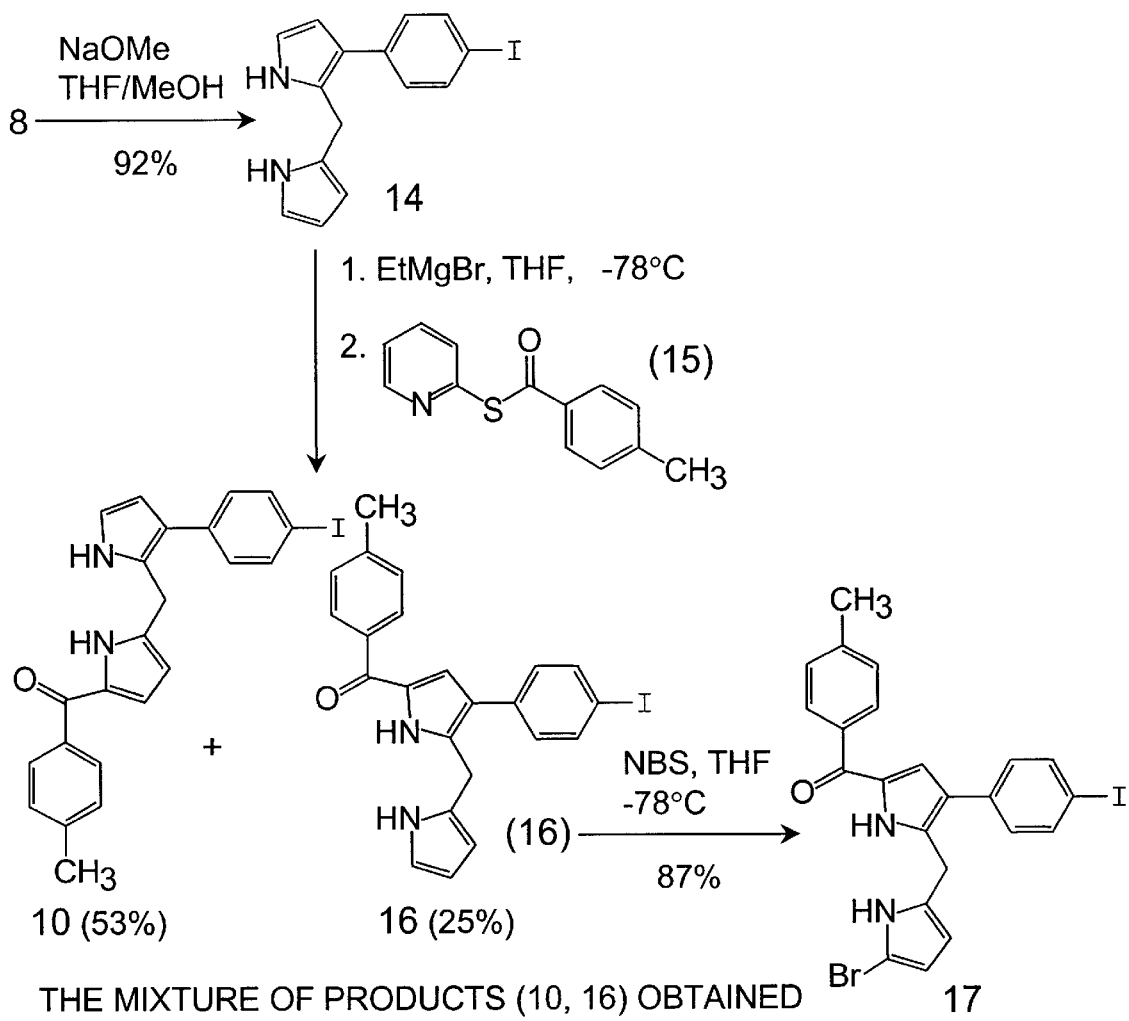
FIG. 15 further illustates the synthesis of β-substituted chlorin eastern half precursors.
Figure 15:
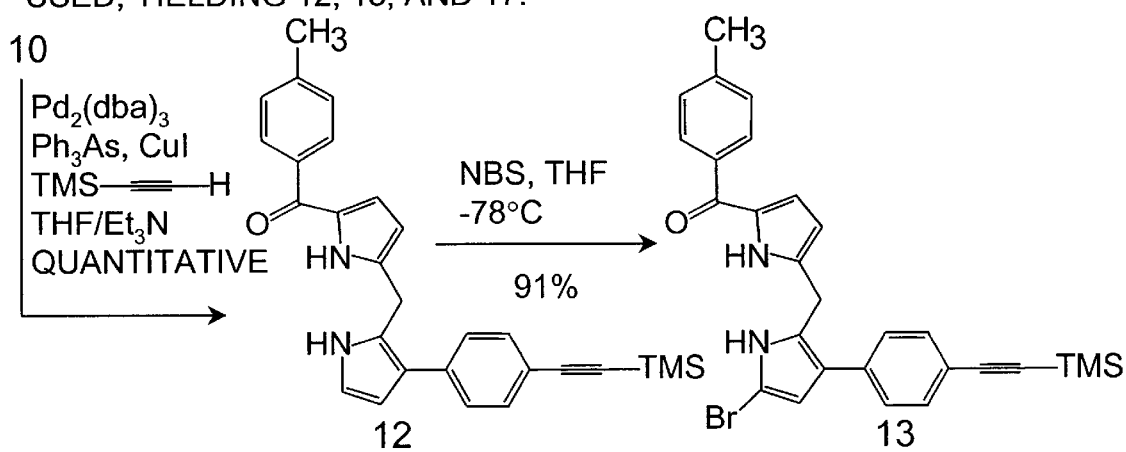

A second β-substituted dipyrromethane was prepared by Sonogashira coupling (Sonogashira, K. et al., *Tetrahedron Lett.* 1975, 4467–4470) of iodophenyl-substituted 10 with trimethylsilylacetylene. In this manner the trimethylsilylethynyl dipyrromethane 12 was obtained in quantitative yield (FIG. 15). Reaction of 12 with NBS at –78 ° C. furnished the corresponding bromodipyrromethane 13 in 91% yield.

The preparation of a dipyrromethane bearing a substituent at a different β site using the same BOC protected dipyrromethane 8 was also sought reversing the order of acylation and deprotection that led to 10. Thus, deprotection of 8 with NaOMe/MeOH afforded the β-substituted dipyrromethane 14 (FIG. 15). A procedure was recently devised for the selective mono-acylation of meso-substituted dipyrromethanes using EtMgBr and an S-pyridyl substituted benzothioate (Rao, P. D.; Dhanalekshmi, S.; Littler, B. J.; Lindsey, J. S. *J. Org. Chem.* submitted). Application of this monoacylation method to 14 resulted in a mixture of two regioisomers (10, 16). Attempts to obtain 16 as the major product by varying the experimental conditions were unsuccessful. Separation of the two regioisomers was difficult and required extensive flash column chromatography. The minor isomer 16 was obtained in 25% yield. Treatment of 16 with 1 equivalent of NBS in THF at –78° C. yielded 17 in 87% yield as a yellow solid. All β-substituted 1-bromodipyrromethanes (11, 13, 17) are somewhat unstable but remain intact for a few weeks upon storage at 0° C. under argon.

Synthesis of a β-substituted Western Half.

Figure 16:
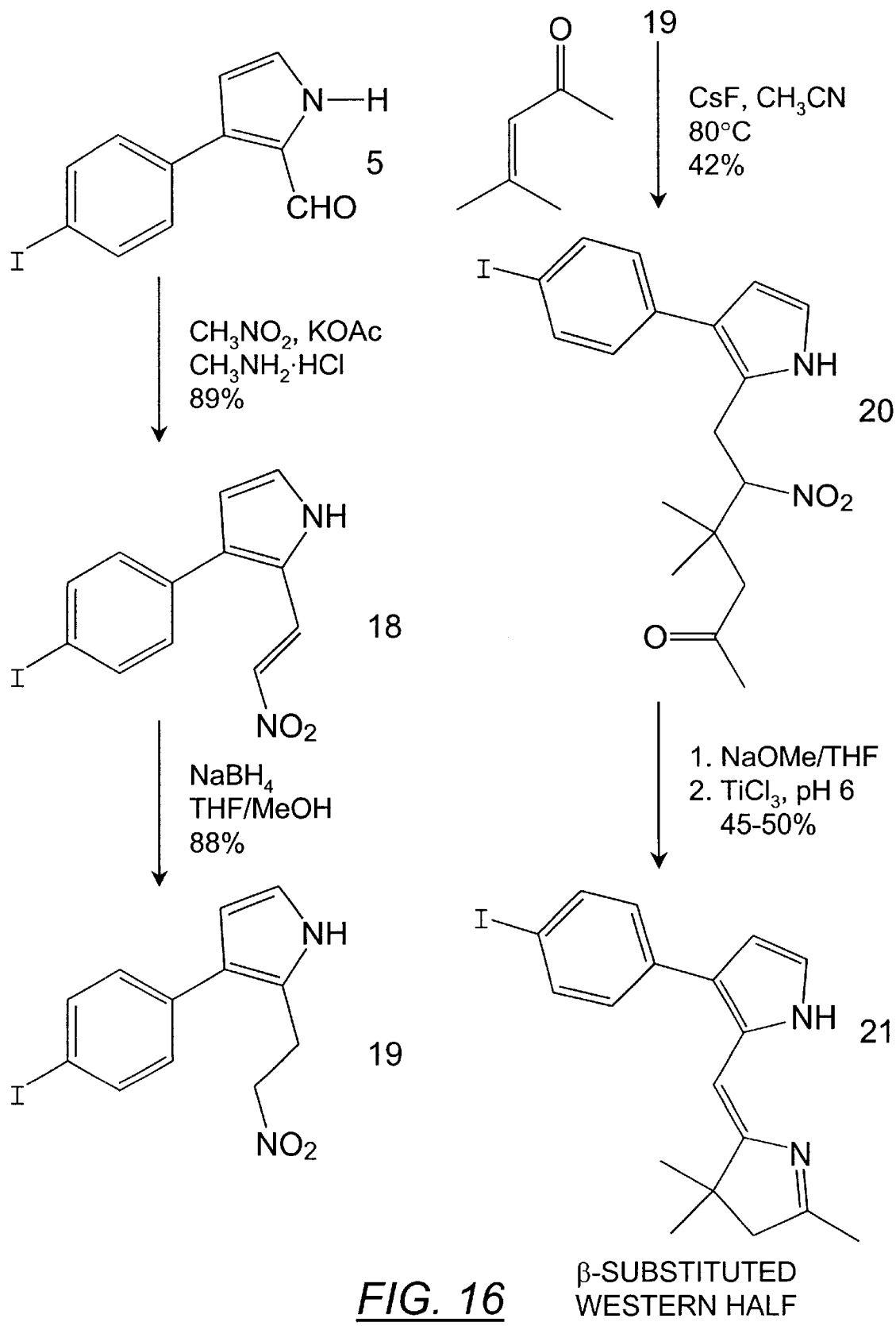
FIG. 16 illustrates the synthesis of a β-substituted chlorin western half (WH).

The synthesis of a Western half lacking any β-substituents except for the geminal dimethyl group (1) was previously developed (Strachan, J. P. et al., *J. Org. Chem.* 2000, 65, 3160–3172). Pyrrole-carboxaldehyde 5, available in multigram quantities, provided a convenient starting point for the synthesis of a new Western half bearing a synthetic handle at a β position. A β-substituted Western half in conjunction with the β-substituted Eastern half would enable the synthesis of chlorin building blocks bearing two β substituents positioned at opposite sides of the macrocycle. Application of the reaction conditions used to obtain 2-(2-nitrovinyl) pyrrole from 2-formylpyrrole (Strachan, J. P.; O'Shea, D. F.; Balasubramanian, T.; Lindsey, J. S. *J. Org. Chem.* 2000, 65, 3160–3172) to the reaction of 5 resulted largely in recovery of starting material. After a limited study, it was found that treatment of 5 with KOAc and a slight excess of methylamine-hydrochloride in nitromethane (instead of methanol) as solvent at room temperature for 2 h (instead of 16 h) yielded the desired aldol-condensation product 18 in 89% yield (FIG. 16). It is noteworthy that a longer reaction time led to the formation of the Michael addition product of nitromethane at the nitrovinyl group in 18, forming 2-(1,3-dinitro-2-propyl)-3-(4-iodophenyl)pyrrole in ~30% yield. NaBH$_4$ reduction of 18 gave 19, which underwent Michael addition with mesityl oxide in the presence of CsF at 80° C. to give the nitro-hexanone product 20, the precursor to the β-substituted Western half. Although the Michael addition was fast compared to that forming the β-unsubstituted counterpart (precursor to 1), the yield was slightly lower (42% vs. 65%). Treatment of 20 with NaOMe followed by a buffered TiCl$_3$ solution yielded the β-substituted Western half 21 in 45–50% yield as a light green solid. The yield and stability of the β-substituted WH is greater than that of the unsubstituted analog (21 has mp=141–142° C.; 1 is an oil).

Chlorin Formation.

Figure 17:
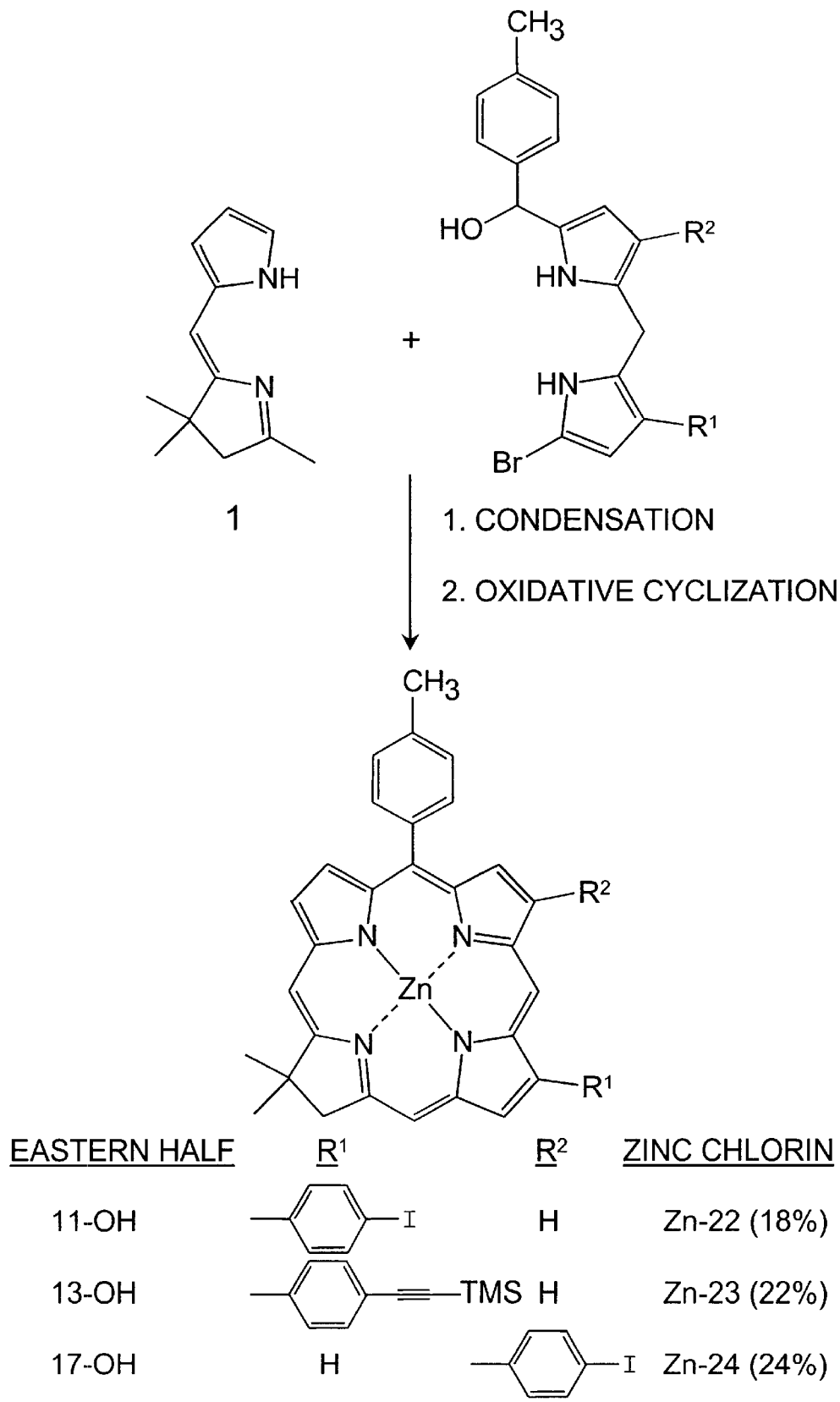
FIG. 17 illustrates the synthesis of a β-substituted chlorin.

Prior synthesis of chlorins involved (1) formation of the bromodipyrromethane-monocarbinol (2-OH, EH) by reduction of the carbonyl group in the EH precursor, (2) acid-catalyzed condensation of the EH and WH (1) to obtain the dihydrobilene-α, and (3) oxidative metal-mediated cyclization to give the chlorin (Strachan, J. P.; O'Shea, D. F.; Balasubramanian, T.; Lindsey, J. S. *J. Org Chem.* 2000, 65, 3160–3172). All the three steps are done in succession on the same day. This same procedure was employed herein except that the workup conditions are different due to the labile nature of the β-substituted EH precursors (11, 13, 17) and corresponding β-substituted Eastern halves. In a typical reaction, 11 was treated with NaBH$_4$ in THF/MeOH (4:1) at room temperature under argon. Upon the disappearance of starting material (TLC analysis), the reaction mixture was worked up and the carbinol 11-OH was treated with 1.2 equivalents of WH 1 at room temperature in $CH_3CN$ containing TFA. After 25–30 minutes the resulting dihydrobilene-α was obtained by quenching the reaction mixture with aqueous $NaHCO_3$ and workup in $CH_2Cl_2$. Anhydrous toluene and 15 molar equivalents each of $AgIO_3$, $Zn(OAc)_2$ and piperidine were added, and the mixture was heated at 80° C. for ~2.5 h. The reaction mixture slowly changed from red to green, indicating the formation of chlorin. Filtration of the reaction mixture through a pad of silica followed by column chromatography afforded the chlorin Zn-22 in >90% purity. Precipitation with $CH_2Cl_2$/hexanes furnished pure chlorin (Zn-22) in 18% yield (FIG. 17). Similar treatment of Eastern half 13-OH and 1 gave the zinc chlorin Zn-23 in 22% yield. The Eastern half (17) bearing a β substituent at position 8 reacted similarly with 1 affording zinc chlorin Zn-24.

Figure 18:
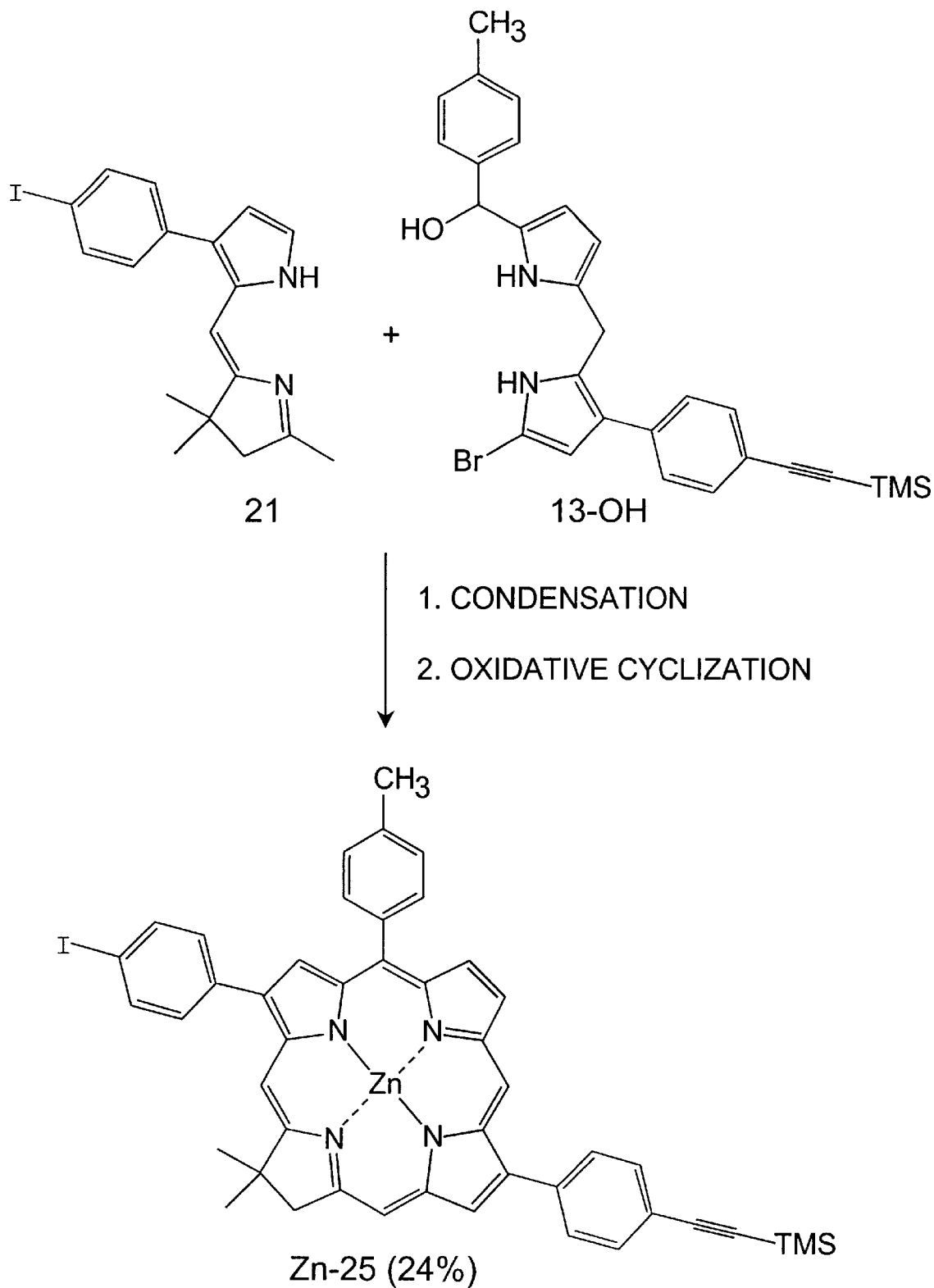
FIG. 18 illustrates the synthesis of a trans β-substituted chlorin.

The chlorins Zn22–24 each bear one β substituent. In order to prepare a chlorin bearing two β substituents, 13-OH and Western half 21 were reacted to give zinc chlorin Zn-25 in 24% yield (FIG. 18). This chlorin has an iodophenyl group and an ethynylphenyl group at β positions on opposite sides of the macrocycle. Porphyrins bearing iodophenyl and ethynylphenyl groups in a trans orientation have been employed in the stepwise synthesis of linear multi-porphyrin arrays (Wagner, R. W.; Lindsey, J. S. *J. Am. Chem. Soc.* 1994, 116, 9759–9760; Wagner, R. W.; Ciringh, Y.; Clausen, P. C.; Lindsey, J. S. *Chem. Mater.* 1999, 11, 2974–2983; Lindsey, J. S. et al., *Tetrahedron* 1994, 50, 8941–8968). Analogous linear multi-chlorin arrays should be attainable with Zn-25.

In each of these chlorin-forming reactions only one chlorin product was obtained, indicating the absence of scrambling during the course of the reaction. This methodology is quite general and the yields of 18–24% obtained with the three β-substituted Eastern halves (11-OH, 13-OH, 17-OH) and the β-substituted Western half (21) are noticeably superior to the ~10% obtained with the meso-substituted Eastern halves (2-OH) and Western half (1).

The Zn-chlorins were demetalated to give the corresponding free base chlorins by treatment with TFA in $CH_2Cl_2$. In most cases the crude product was pure enough for analysis while in other cases the free base chlorin was further purified by a short silica column.

Spectral Properties of the Chlorins.
$^1H$ NMR Spectra.

The NMR spectral information available for chlorins has been obtained largely from naturally occurring chlorins, which bear alkyl groups at most of the β positions. The $^1H$ NMR spectra of β-substituted free base chlorins (22–25) and Zn chlorins (Zn-22-Zn-25) are readily assignable and confirm the expected substitution patterns. In 22, the two NH protons appear as broad peaks at δ –2.15 and –1.85 ppm, and a downfield signal appears for one of the meso substituted protons (assigned to C-10) at δ 9.84 ppm. The reduced ring exhibits a singlet at δ 2.07 ppm (geminal dimethyl groups) and another singlet at δ 4.64 ppm (ring $CH_2$), as also observed in the meso-substituted chlorins. Other characteristic features include an AB quartet at δ 8.85 ppm (β-pyrrole protons of ring A), two doublets at δ 8.64 and 8.90 ppm (β-pyrrole protons of ring B), and singlets at δ 8.91 (for 2H) and 8.99 ppm (two meso protons at C-15 and C-20, and one β-pyrrole proton of ring C). The significant changes for the β-substituted Zn-22 are the absence of signals corresponding to NH protons, and slight upfield shifts of the geminal dimethyl group (δ 2.01 ppm), ring methylene protons (δ 4.48 ppm) and all of the meso and β-pyrrole protons. Similar trends were observed for free base chlorin 23 and zinc chlorin Zn-23.

The $^1H$ NMR spectrum of chlorin 24 is slightly different due to the difference in the substitution pattern at the perimeter of the molecule. Characteristic features in addition to the different chemical shifts of the two NH protons include the singlet at δ 8.64 ppm (β-pyrrole proton of ring B) and the downfield signal at δ 9.17 ppm as a doublet (one of the β-pyrrole protons of ring C). The $^1H$ NMR spectrum of chlorin 25 is more simple. The β-pyrrole protons of ring B appear as two doublets at δ 8.62 and 8.88, and the AB quartet corresponding to the β-pyrrole protons of ring A in chlorins 22–24 is absent. The remaining meso protons and β-pyrrole protons resonate as five singlets. Zn-25 showed a similar pattern except for the slight upfield shift of the peaks due to the meso and β protons.

A distinctive feature of this set of chlorins is that the β-pyrrole protons of ring B appear slightly upfield compared to the other pyrrole protons. This indicates that the β-pyrrole double bond of ring B does not participate as fully in the 18π electron ring current of the chlorin macrocycle.

Absorption Spectra.

Each of the free base chlorins (22–25) exhibits an intense Soret band and a characteristic strong $Q_y$ band. The Soret band in each case exhibited a short-wavelength shoulder of significant intensity, resulting in a fwhm ranging from 32–35 nm for 22–25. A similar spectral feature was observed for the previous set of meso-substituted free base chlorins that were examined. The Soret band red-shifted slightly as the substituent was moved from position 8 (24) to 12 (22, 23) to 2 and 12 (25). Significant differences in $Q_y$ absorption maximum and absorption intensity occurred depending on the site of substitution of the chlorin. The $Q_y$ absorption maximum ranged from 637 to 655 nm, and paralleled the redshift of the Soret band. In addition, a hyperchromic effect of the $Q_y$ band was observed accompanying the bathochromic shift. Although the accurate determination of molar absorption coefficients can be difficult especially with handling small samples, the ratio of the $Q_y$ and Soret bands provides a relative measure of the changing band intensities. The Soret/$Q_y$ band ratio decreases from 4.3 (24) to 2.5 (25). These data are listed in Table 1. It is noteworthy that the chlorins with an iodophenyl or ethynylphenyl group at the 12 position exhibited nearly identical absorption spectra. For comparison, the meso-substituted free base chlorins exhibited absorption maxima at 411–414 nm and 640–644 nm.

Each of the zinc chlorins (Zn-22-Zn-25) exhibits an intense Soret band and a characteristic strong $Q_y$ band. The Soret band in each case was sharp (fwhm 18–21 nm) with only a very weak short-wavelength shoulder. The $Q_y$ band underwent a redshift from 606 nm to 628 nm as the substituent location was changed from 8 (Zn-24) to 12 (Zn-22, Zn-23) to 2 and 12 (Zn-25). A concomitant increase in intensity of the $Q_y$ band also was observed. These results are listed in Table 1. In all of the chlorins examined, a redshift in the Soret band was accompanied by a more pronounced redshift in the $Q_y$ band. The only discrepancy in this trend occurred in comparing Zn-24 and Zn-22 (or Zn-23). The former has the shortest wavelength $Q_y$ band (606 nm) but a Soret band at 415 nm, compared with 615 nm and 411 nm for that of the latter. For comparison, the meso-substituted zinc chlorins exhibited absorption maxima at 412 nm and 608 nm.

Fluorescence Spectra and Yields.

Similar to the meso-substituted chlorins, the free base chlorins 22–24 exhibit a characteristic sharp fluorescence band at 640 nm and a weaker emission in the region 660–720 nm. The latter exhibited two discernible maxima at approximately 680 and 710 nm. The emission spectrum of free base chlorin 25 was shifted to 660 nm and 726 nm. The Zn chlorins Zn-22 and Zn-23 each exhibit a sharp fluorescence band at around 620 nm and a weak band at 676 mn, whereas the emission of Zn-24 appears at 609 and 661 nm. The emission spectrum of Zn-25 is more red shifted as observed in free base 25 (635 and 691 nm). The fluorescence quantum yields were determined for those chlorins lacking iodophenyl substituents (which exhibit decreased yields due to the heavy atom effect). The fluorescence quantum yield of free base chlorin 23 was 0.25, while that of Zn-23 was 0.11. These values are in line with those of other naturally occurring or synthetic chlorins.

Conclusions.

The synthesis of chlorins described herein provides the following features: (1) control over the location of the reduced ring, (2) locking in of the chlorin hydrogenation level through use of a geminal dimethyl group, (3) location of synthetic handles at designated sites at the perimeter of the macrocycle, and (4) a single chlorin product thereby facilitating purification. The ability to incorporate substituents at distinct locations (2, 5, 8, 10, or 12) about the chlorin perimeter opens a number of opportunities. With different substitution patterns, the $Q_y$ absorption band can be tuned over the range 637–655 nm for free base chlorins and 606–628 nm for zinc chlorins, enabling greater spectral coverage. The chlorin bearing synthetic handles at the 2 and 12 positions (25) should enable the incorporation of chlorin building blocks into linear architectures. The availability of a family of synthetic chlorins bearing diverse substituents at defined locations should facilitate the systematic study of substituent effects and broaden the scope of chlorin containing model systems.

Experimental Section

General.

$^1$H and $^{13}$C NMR spectra (300 MHz) were obtained in CDCl$_3$ unless noted otherwise. Absorption spectra (Cary 3, 0.25 nm data intervals) and fluorescence spectra (Spex FluoroMax, 1 nm data intervals) were collected routinely. Chlorins were analyzed in neat form by laser desorption mass spectrometry (LD-MS) in the absence of a matrix (Fenyo, D. et al., *J. Porphyrins Phthalocyanines* 1997, 1, 93–99; Srinivasan, N. et al., *J. Porphyrins Phthalocyanines* 1999, 3, 283–291). Pyrrole was distilled at atmospheric pressure from CaH$_2$. Melting points are uncorrected. p-Iodobenzaldehyde was obtained from Karl Industries. All other reagents and starting materials were obtained from Aldrich. Spectral parameters including molar absorption coefficients and fluorescence quantum yields ($\Phi_f$) were determined as previously described (Strachan, J. P. et al., *J. Org. Chem.* 2000, 65, 3160–3172).

Chromatography.

Preparative chromatography was performed using silica (Baker) or alumina (Fisher A540, 80–200 mesh) and eluting solvents based on hexanes admixed with ethyl acetate or CH$_2$Cl$_2$.

Solvents.

THF was distilled from sodium benzophenone ketyl as required. CH$_3$CN (Fisher certified A.C.S.) was distilled from CaH$_2$ and stored over powdered molecular sieves. Nitromethane was stored over CaCl$_2$. CH$_2$Cl$_2$ was distilled from CaH$_2$. Dry methanol was prepared as follows. Magnesium turnings (5 g) and iodine (0.5 g) with 75 mL of methanol were warmed until the iodine disappeared and all the magnesium was converted to the methoxide. Up to 1 L of methanol was added and heated at reflux for a minimum of 2 h before collecting. Other solvents were used as received.

Compounds 1 (Strachan, J. P. et al., *J. Org. Chem.* 2000, 65, 3160–3172) and 3 (Balasubramanian, T.; Lindsey, J. S. Tetrahedron 1999, 55, 6771–6784) were prepared according to literature procedures.

3-(4-Iodophenyl)pyrrole (4).

Following earlier procedures (Balasubramanian, T.; Lindsey, J. S. *Tetrahedron* 1999, 55, 6771–6784), a mixture of 3-ethoxycarbonyl-4-(4-iodophenyl)pyrrole (7.20 g, 21.1 mmol) and ethylene glycol (55 mL) in a 100-mL Claisen flask was flushed with argon for 10 min and powdered NaOH (2.2 g, 55 mmol) was then added. The flask was placed in an oil bath at 120 ° C. and the oil bath temperature was raised to 160° C. After 2.5 h, the flask was cooled to room temperature and treated with 10% aq NaCl (100 mL). The aqueous layer was extracted with CH$_2$Cl$_2$, the organic layers were collected, washed with 10% aq NaCl, dried (Na$_2$SO$_4$), concentrated, and recrystallized in ethanol affording light brown crystals (5.18 g, 91%). mp 164–165° C.; $^1$H NMR γ 6.51 (m, 1H), 6.83 (m, 1H), 7.08 (s, 1H), 7.27 (d, J=8.7 Hz, 2H), 7.63 (d, J=8.7 Hz, 2H); $^{13}$C NMR δ 89.9, 106.3, 114.7, 119.1, 123.8, 127.0, 135.2, 137.5; EI-MS obsd 268.9702, calcd 268.9702. Anal. Calcd for C$_{10}$H$_8$IN: C, 44.6; H, 3.0; N, 5.2. Found: C, 44.7; H, 3.0; N, 5.1. The synthesis starting from 4-iodobenzaldehyde (35 g), monoethyl malonate, and TosMIC has been performed with linear scale up of the established procedures, affording 21.5 g of 4.

2-Formyl-3-(4-iodophenyl)pyrrole (5).

A solution of 4 (5.15 g, 19.1 mmol) in DMF (6.1 mL) and CH$_2$Cl$_2$ (140 mL) under argon was cooled to 0° C. and then POCl$_3$ (2.11 mL, 22.6 mmol) was added dropwise. After 1 h, the flask was warmed to room temperature and stirred overnight. The reaction was quenched at 0° C. with 2.5 M NaOH (100 mL). The mixture was poured into water (500 mL), extracted with CH$_2$Cl$_2$, and the combined organic layers were washed with water, brine, dried (Na$_2$SO4), and the solvent was removed in vacuo. $^1$H NMR spectroscopy showed two regioisomers in a ~6:1 ratio. The minor isomer exhibited signals at δ 7.21 and 7.39 ppm, compared with signals at δ 6.42 and 7.14 for the major isomer. The most downfield signal (7.39 ppm) is assigned to the proton adjacent to a formyl group, which occurs in the 2-formyl-4-aryl substituted pyrrole. Recrystallization from ethyl acetate afforded an orange solid corresponding to the major aldehyde (2.25 g). The mother liquor was concentrated and purified by flash column chromatography [silica, hexanes/ ethyl acetate (3:1)]. The first fraction corresponded to the major aldehyde (1.25 g). The total yield of the title compound was 3.50 g (62%): mp 153–154 ° C.; $^1$H NMR δ 6.42 (m, 1H), 7.14 (m, 1H), 7.22 (m, 2H), 7.76 (m 2H), 9.59 (s, 1H), 10.72 (br, 1H); $^{13}$C NMR δ 93.5, 104.3, 111.4, 125.8, 128.6, 130.8, 133.1, 137.8, 179.4; FAB-MS obsd 296.9663, calcd 296.9651; Anal. Calcd for C$_{10}$H$_8$INO: C, 44.5; H, 2.7; N, 4.7. Found: C, 44.4; H, 2.7; N, 4.6.

N-tert-Butoxycarbonyl-2-formyl-3-(4-iodophenyl)pyrrole (6).

Following a standard procedure (Tietze, L. F.; Kettschau, G.; Heitmann, K. *Synthesis* 1996, 851–857), sample of NaH (70 mg, 1.75 mmol, 60% dispersion in mineral oil) in a round-bottomed flask under argon was washed twice with anhydrous pentane (~5 mL). Anhydrous THF (14 mL) was added followed by 5 (400 mg, 1.35 mmol). After stirring for 30 min at room temperature, (BOC)$_2$O (325 mg, 1.5 mmol) was added and stirring was continued for another 2 h. The reaction was quenched with 50% satd. aq NH$_4$Cl (50 mL).

The mixture was extracted with ether, and the combined organic layers were washed with brine, dried ($Na_2SO_4$), and filtered [silica, hexanes/ethyl acetate (4:1)] to yield a viscous oil (535 mg, quantitative). $^1$H NMR δ 1.64 (s, 9H), 6.33 (d, J=3.0 Hz, 1H), 7.30 (d, J=8.1 Hz, 2H), 7.46 (d, J=3.0 Hz, 1H), 7.72 (d, J =8.1 Hz, 2H), 10.22 (s, 1H); $^{13}$C NMR δ 27.7, 85.8, 94.2, 113.2, 126.7, 128.5, 131.3, 132.8, 137.0, 137.4, 148.3, 181.6; FAB-MS obsd 397.0176, calcd 397.0175 ($C_{16}H_{16}INO_3$).

N-tert-Butoxycarbonyl-2-hydroxymethyl-3-(4-iodophenyl) pyrrole (7).

A solution of 6 (400 mg, 1.0 mmol) in anhydrous THF (12 mL) under argon was cooled to −20 to −25° C. and $LiBH_4$ (55 mg, 2.5 mmol) was added in portions. The reaction was monitored by TLC (silica, hexanes/ethyl acetate (4:1)), and when no starting material was detected (20–25 min), the reaction was quenched with cold water (30 mL). The aqueous layer was extracted with $CH_2Cl_2$ and the organic layer was dried ($Na_2SO_4$), concentrated, and purified by flash column chromatography [silica, hexanes/ethyl acetate containing 1% $Et_3N$ (3:1)] yielding a gum (330 mg, 82%). $^1$H NMR δ 1.62 (s, 9H), 3.61 (br, 1H), 4.66 (d, J=7.2 Hz, 2H), 6.25 (d, J=3.6 Hz, 1H), 7.18 (d, J=8.1 Hz, 2H), 7.22 (d, J=3.6 Hz, 1H), 7.71 (d, J=8.1 Hz, 2H); $^{13}$C NMR δ 27.8, 55.3, 84.7, 92.4, 111.2, 121.3, 127.9, 130.0, 130.4, 134.1, 137.5, 149.8; FAB-MS obsd 399.0336, calcd 399.0331 ($C_{16}H_{18}INO_3$).

3-(4-Iodophenyl)-10-N-(tert-butoxycarbonyl) dipyrromethane (8).

A solution of 7 (1.2 g, 3.0 mmol) and pyrrole (3.36 mL, 48 mmol) in 1,4-dioxane (36 mL) at room temperature was treated with 10% aq HCl (6.0 mL). The reaction was monitored by TLC [silica, hexanes/ethyl acetate (4:1)]. After 4 h, satd aq $NaHCO_3$ (50 mL) and water (50 mL) were added and the mixture was extracted with $CH_2Cl_2$. The combined organic layers were washed with water, brine, dried ($Na_2SO_4$), concentrated, and purified by flash chromatography [silica, hexanes/ethyl acetate (4:1)]. A non-polar product was isolated in minor amount (uncharacterized). The desired product was obtained as a pale brown solid (920 mg, 68% yield): mp 128–129 ° C.; $^1$H NMR δ 1.57 (s, 9H), 4.18 (s, 2H), 5.87 (br, 1H), 6.10 (m, 1H), 6.22 (d, J=3.0 Hz, 1H), 6.64 (m, 1H), 7.16 (d, J=8.0 Hz, 2H), 7.24 (d, J=3.6 Hz, 1H), 7.71 (d, J=8.0 Hz, 2H), 8.78 (br, 1H); $^{13}$C NMR δ24.6, 27.8, 84.3, 92.1, 105.8, 107.9, 111.6, 116.3, 121.0, 126.8, 128.5, 130.4, 130.8, 135.0, 137.4, 150.0; FAB-MS obsd 448.0659, calcd 448.0648; Anal. Calcd for $C_{20}H_{21}IN_2O_2$: C, 53.6; H, 4.7; N, 6.3. Found: C, 54.1; H, 4.9; N, 5.9.

3-(4-Iodophenyl)-9-(4-methylbenzoyl)-10-N-(tert-butoxycarbonyl)dipyrromethane (9).

A solution of 8 (448 mg, 1.0 mmol) in anhydrous THF (15 mL) under argon at 0° C. was treated slowly with EtMgBr (1 M in THF, 2.5 mL, 2.5 mmol). The mixture was stirred for 30 minutes at 0° C., then, p-toluoyl chloride (200 μL, 1.5 mmol) was added slowly and stirring was continued for 1 h at 0° C. The reaction was quenched with satd. aq $NH_4Cl$ and extracted with $CH_2Cl_2$. The combined organic layers were washed with water, brine, dried ($Na_2SO_4$), concentrated, and the product was purified by flash column chromatography [silica, hexanes/ethyl acetate (4:1)]. The product was obtained as a pale white solid (375 mg, 66%): mp 120–121° C.; (due to possible rotamers the $^1$H NMR and $^{13}$C NMR are not very clean) $^1$H NMR δ 1.56 (s, 9H), 2.42 (s, 3H), 4.29 (s, 2H), 5.95 (m, 1H), 6.26 (m, 1H), 6.76 (m, 1H), 7.09 (m, 2H), 7.16 (m, 1H), 7.25 (m, 2H), 7.31 (m, 1H), 7.71 (d, 8.7 Hz, 2H), 7.77 (d, J=8.1 Hz, 2H), 9.95 (br, 1H); $^{13}$C NMR δ 25.2, 27.8, 31.7, 84.8, 92.3, 109.3, 111.5, 119.6, 121.5, 125.8, 126.3, 128.9, 129.0, 130.2, 130.6, 134.7, 135.8, 137.5, 138.6, 142.0, 149.7, 183.8; Anal. Calcd for $C_{28}H_{27}IN_2O_3$: C, 59.4; H, 4.8; N, 5.0. Found: C, 59.4; H, 4.6; N, 5.1.

3-(4-Iodophenyl)-9-(4-methylbenzoyl)dipyrromethane (10).

Following a standard method for the deprotection of BOC-protected pyrroles (Hasan, I. et al., *J. Org. Chem.* 1981, 46, 157–164), a solution of 9 (328 mg, 0.58 mmol) in anhydrous THF (4 mL) under argon at room temperature was treated with methanolic NaOMe (0.7 mL, prepared by dissolving 200 mg of NaOMe in 1.0 mL of MeOH). After 20–25 min, the reaction was quenched with a mixture of hexanes and water (20 mL, 1:1) and extracted with ethyl acetate. The combined organic layers were washed with water, brine, dried ($Na_2SO_4$), and purified by flash column chromatography [silica, hexanes/ethyl acetate (3:1)] to yield a pale brown solid (216 mg, 80%): mp 185–186 ° C.; $^1$H NMR δ 2.43 (s, 3H), 4.17 (s, 2H), 6.15 (m, 1H), 6.56 (m, 1H), 6.85 (m, 1H), 7.17 (m, 2H), 7.28 (m, 2H), 7.69 (m, 2H), 7.77 (d, J=7.8 Hz, 2H), 9.43 (br, 1H), 10.88 (br, 1H); $^{13}$C NMR δ21.6, 25.2, 90.6, 108.6, 110.3, 117.4, 121.1, 122.3, 123.9, 129.0, 129.1, 130.0, 130.7, 135.5, 136.2, 137.4, 139.4, 142.6, 185.2; FAB-MS obsd 466.0561, calcd 466.0542; Anal. Calcd for $C_{23}H_{19}IN_2O$: C, 59.2; H, 4.1; N, 6.0. Found: C, 59.3; H, 4.2; N, 5.9.

1-Bromo-3-(4-iodophenyl)-9-(4-methylbenzoyl) dipyrromethane (11).

Following earlier procedures (Strachan, J. P. et al., *J. Org. Chem.* 2000, 65, 3160–3172), 10 (120 mg, 0.26 mmol) was dissolved in anhydrous THF (6 mL) and cooled to −78° C. under argon. Recrystallized NBS (46 mg, 0.26 mmol) was added and the reaction mixture was stirred for 1 h (−78° C.) and then quenched with a mixture of hexanes and water (20 mL, 1:1) and allowed to warm to 0° C. The aqueous portion was extracted with reagent-grade ether and the combined organic layers were dried over $K_2CO_3$. The solvent was evaporated under vacuum at room temperature. Purification by flash column chromatography [silica, hexanes/ether (2:1)] afforded a yellow solid (120 mg, 85%). The bromodipyrromethane is unstable but can be stored for several weeks at 0° C. mp 160° C. (decomp); $^1$H NMR δ 2.44 (s, 3H), 4.09 (s, 2H), 6.12 (d, J=3.0 Hz, 1H), 6.16 (m, 1H), 6.89 (m, 1H), 7.14 (d, J=7.8 Hz, 2H), 7.30 (d, J=7.8 Hz, 2H), 7.71 (d, J=8.1 Hz, 2H), 7.80 (d, J=8.1 Hz, 2H), 10.33 (br, 1H), 11.59 (br, 1H); $^{13}$C NMR δ 21.6, 24.9, 91.1, 97.9, 110.2, 110.5, 122.8, 123.5, 125.4, 129.2, 130.2, 130.0, 130.8, 135.2, 135.4, 137.5, 139.9, 142.8, 186.1; FAB-MS obsd 543.9642, calcd 543.9647; Anal. Calcd for $C_{23}H_{18}BrIN_2O$: C, 50.7; H, 3.3; N, 5.1. Found: C, 51.3; H, 3.5; N, 5.2.

3-[4-(Trimethylsilylethynyl)phenyl]-9-(4-methylbenzoyl) dipyrromethane (12).

Samples of 10 (279 mg, 0.599 mmol), $Pd_2(dba)_3$ (42 mg, 0.046 mmol), $Ph_3As$ (113 mg, 0.369 mmol), and CuI (9 mg, 0.047 mmol) were added to a 25-mL Schlenk flask. The flask was evacuated and purged with argon for three times. Then deaerated anhydrous $THF/Et_3N$ (6 mL, 1:1) was added and followed by trimethylsilylacetylene (127 μL, 0.90 mmol). The flask was sealed, immersed in an oil bath (37° C.), and the mixture was stirred overnight. Then $CH_2Cl_2$ (20 mL) was added and the mixture was filtered through a pad of Celite, washed several times with $CH_2Cl_2$, concentrated, and the residue was purified by flash column chromatography [silica, hexanes/ethyl acetate (3:1)] to afford a yellow solid (262 mg, quantitative): mp 126–127° C.; $^1$H NMR δ 0.26 (s, 9H), 2.43 (s, 3H), 4.19 (s, 2H), 6.16 (m, 1H), 6.28 (m, 1H), 6.55 (m, 1H), 6.85 (m, 1H), 7.28 (d, J=8.7 Hz, 2H), 7.38 (d, J=8.1 Hz, 2H), 7.49 (d, J=8.7 Hz, 2H), 7.77 (d, J=8.1 Hz, 2H), 9.51 (br, 1H), 10.96 (br, 1H); $^{13}$C NMR δ 0.0, 21.5, 25.3, 105.4, 108.6, 110.3, 117.4, 119.9, 121.5, 122.3, 124.1, 127.6, 129.0, 129.1, 130.7, 132.0, 135.5, 137.0, 139.5, 142.6, 185.2; FAB-MS obsd 436.1972, calcd 436.1971; Anal. Calcd for $C_{28}H_{28}N_2OSi$: C, 77.0; H, 6.5; N, 6.4. Found: C, 76.3; H, 6.3; N, 6.3.

1-Bromo-3-[4-(trimethylsilylethynyl)phenyl]-9-(4-methylbenzoyl)dipyrromethane (13).

Following the procedure for the synthesis of 11, treatment of 12 (150 mg, 0.34 mmol) with NBS (60 mg, 0.34 mmol) afforded a pale yellow solid (160 mg, 91%): mp 140° C. (decomp); $^1$H NMR δ 0.26 (s, 9H), 2.44 (s, 3H), 4.12 (s, 2H), 6.17 (m, 2H), 6.89 (m, 1H), 7.31 (m, 4H), 7.50 (d, J=9.0 Hz, 2H), 7.80 (d, J=8.1 Hz, 2H), 10.16 (br, 1H), 11.42 (br, 1H); $^{13}$C NMR δ 0.0, 21.5, 25.0, 94.1, 97.9, 105.2, 110.3, 110.5, 120.4, 123.3, 125.5, 127.7, 129.2, 130.7, 132.1, 135.4, 135.9, 139.7, 142.8, 185.9; FAB-MS obsd 514.1079, calcd 514.1076; Anal. Calcd for $C_{28}H_{27}BrN_2OSi$: C, 65.2; H, 5.3; N, 5.4. Found: C, 65.1; H, 5.2; N, 5.3.

3-(4-Iodophenyl)dipyrromethane (14).

Following the deprotection procedure used to prepare 10, a sample of 8 (225 mg, 0.50 mmol) in anhydrous THF (4 mL) under argon at room temperature was treated with methanolic NaOMe (0.6 mL, prepared by dissolving 200 mg of NaOMe in 1.0 mL of MeOH). After 15 min, the reaction was quenched with mixture of hexanes and water (14 mL, 1:1), extracted with ethyl acetate, and the combined organic layers were washed with water, brine, then dried over $Na_2SO_4$. The residue was passed through a filtration column to yield a light brown solid (160 mg, 92%). Analytical data are in accord with the literature (Balasubramanian, T.; Lindsey, J. S. *Tetrahedron* 1999, 55, 6771–6784).

3-(4-Iodophenyl)-1-(4-methylbenzoyl)dipyrromethane (16).

Following a general monoacylation procedure for unprotected dipyrromethanes (Rao, P. D. et al., *J. Org. Chem.* 2000, 65, 1084–1092.), EtMgBr (1 M solution in THF, 2.2 mL, 2.2 mmol) was added to a solution of 14 (385 mg, 1.1 mmol) in anhydrous THF (14 mL). After stirring for 10 min, the flask was cooled to −78° C. and a solution of pyridyl thioester 15 (255 mg, 1.1 mmol) in anhydrous THF (3 mL) was added slowly. After a few min the cooling bath was removed, stirring was continued for 1 h, then the mixture was quenched with satd aq $NH_4Cl$, water, and then extracted with $CH_2Cl_2$. The combined organic layers were washed with water, brine, dried ($Na_2SO_4$), and concentrated. The two regioisomers formed were purified by two successive flash columns [silica, hexanes/ethyl acetate (3:1)], affording the minor isomer 16 (130 mg, 25%) and the major isomer 10 (270 mg, 53%). Data for 16: mp 190° C. (decomp); 1H NMR δ 2.43 (s, 3H), 4.15 (s, 2H), 6.05 (m, 1H), 6.13 (m, 1H), 6.58 (m, 1H), 6.94 (m, 1H), 7.19 (d, J=8.7 Hz, 2H), 7.28 (d, J=8.1 Hz, 2H), 7.73 (d, J=8.7 Hz, 2H), 7.78 (d, J=8.1 Hz, 2H), 9.17 (br, 1H), 10.83 (br, 1H); $^{13}$C NMR δ21.6, 25.2, 91.8, 106.8, 108.3, 117.8, 121.1, 124.3, 127.2, 129.1, 129.2, 129.7, 130.2, 134.6, 135.4, 136.3, 137.6, 142.9, 185.4; FAB-MS obsd 466.0573, calcd 466.0542; Anal. Calcd for $C_{23}H_{19}IN_2O$: C, 59.2; H, 4.1; N, 6.0. Found: C, 59.1; H, 4.2; N, 5.8.

9-Bromo-3-(4-iodophenyl)-1-(4-methylbenzoyl)dipyrromethane (17).

Following the procedure for the synthesis of 11, treatment of 16 (186 mg, 0.400 mmol) with NBS (72 mg, 0.405mmol) gave a pale yellow solid (189 mg, 87%): mp 140° C. (decomp); $^1$H NMR δ 2.43 (s, 3H), 4.08 (s, 2H), 5.94 (m, 1H), 6.00 (m, 1H), 6.96 (d, J=2.1 Hz, 1H), 7.18 (d, J=8.7Hz, 2H), 7.29 (d, J=8.1 Hz, 2H), 7.74 (d, J =8.7 Hz, 2H), 7.80 (d, J=8.1 Hz, 2H), 9.80 (br, 1H), 11.53 (br, 1H); $^{13}$C NMR was attempted in $CDCl_3$ but the compound decomposed upon lengthy data acquisition. FAB-MS obsd 543.9628, calcd 543.9647; Anal. Calcd for $C_{23}H_{19}IN_2O$: C, 50.7; H, 3.3; N, 5.1. Found: C, 51.2; H, 3.4; N, 5.0.

2-(2-trans-Nitrovinyl)-3-(4-iodophenyl)pyrrole (18).

A mixture of 5 (1.485 g, 5.00 mmol), KOAc (492 mg, 5.01 mmol), methylamine-hydrochloride (402 mg, 5.95 mmol), and nitromethane (45 mL) under argon was stirred at room temperature. The mixture slowly became orange and yielded an orange-red precipitate. The reaction was monitored by TLC and after stirring for 2 h, the TLC showed the appearance of a new component and the disappearance of 5. (A longer reaction time (10 h) led to formation of the Michael addition product, 2-(1,3-dinitro-2-propyl)-3-(4-iodophenyl)pyrrole, in 30% yield.) The reaction was quenched with brine, extracted with ethyl acetate, and the organic layers were dried ($Na_2SO_4$) and concentrated. The residue was treated with hot ethyl acetate and filtered, then concentrated and dissolved in hot $CH_2Cl_2$, followed by precipitation upon adding cold hexanes, affording an orange solid (1.52 g, 89%): mp 217–218° C. ( decomp); $^1$H NMR (acetone-$d_6$) δ 6.56 (d, J=2.1 Hz, 1H), 7.32 (d, J=8.2 Hz, 2H), 7.35 (m, 1H), 7.81 (d, J=13.5 Hz, 1H), 7.90 (d, J=8.3 Hz, 2H), 7.99 (d, J=13.4 Hz, 1H); $^{13}$C NMR (acetone-$d_6$) δ 93.4, 112.5, 121.3, 127.1, 127.2, 128.4, 131.8, 132.8, 135.4, 138.9; FAB-MS obsd 339.9720, calcd 339.9709. Anal. Calcd for $C_{12}H_9IN_2O_2$: C, 42.4; H, 2.7; N, 8.2. Found: C, 41.8; H, 2.6; N, 7.9; $\lambda_{abs}$ (toluene) 395 nm.

2-(2-Nitroethyl)-3-(4-iodophenyl)pyrrole (19).

Following the procedure for a β-unsubstituted pyrrole (Strachan, J. P. et al., *J. Org. Chem.* 2000, 65, 3160–3172), a sample of 18 (1.36 g, 4.00 mmol) was dissolved in anhydrous THF/MeOH (40 mL, 9:1) under argon at 0° C. $NaBH_4$ (605 mg, 16.00 mmol) was added in portions and stirring was continued for 1 h at 0° C. Then the mixture was stirred for 2 h at room temperature. The reaction mixture was neutralized with acetic acid (pH=7), then water (50 mL) was added and the mixture was extracted with ethyl acetate. The combined organic layers were washed with water, brine, dried ($Na_2SO_4$), concentrated, and purified by passage through a short column [silica, hexanes/ethyl acetate (3:1)] to give a pale white solid (1.2 g, 88%): mp 88–89° C.; $^1$H NMR δ 3.41 (t, J=6.6 Hz, 2H), 4.52 (t, J=6.6 Hz, 2H), 6.26 (s, 1H), 6.74 (s, 1H), 7.07 (d, J=8.1 Hz, 2H), 7.69 (d, J=8.1 Hz, 2H), 8.33 (br, 1H); 13C NMR δ24.0, 75.0, 91.1, 109.3, 117.8, 122.1, 122.2, 129.8, 135.7, 137.7; FAB-MS obsd 341.9877, calcd 341.9865; Anal. Calcd for $Cl_2H_{11}IN_2O_2$: C, 42.1; H, 3.2; N, 8.2. Found: C, 42.3; H, 3.3; N, 8.1.

1-[3-(4-Iodophenyl)pyrro-2-yl]-2-nitro-3,3-dimethyl-5-hexanone (20).

Following the procedure for a β-unsubstituted pyrrole (Strachan, J. P. et al., *J. Org. Chem.* 2000, 65, 3160–3172), a mixture of 19 (1.03 g, 3.0 mmol), CsF (2.28 g, 15.0 mmol), and mesityl oxide (1.72 mL, 15.0 mmol) in anhydrous acetonitrile (22.5 mL) was heated at 80° C. for 2.5 h to 3 h, during which the mixture turned from colorless to brown and then dark red. TLC analysis confirmed the absence of starting material. The solvent was evaporated under vacuum, the residue was taken up in ethyl acetate and filtered through a pad of silica using ethyl acetate as eluant. The solvent was evaporated under vacuum and the product was purified by a gravity column [alumina, hexanes/ethyl acetate (2:1)] followed by recrystallization from $CH_2Cl_2$/hexanes to afford brown crystals (550 mg, 42%): mp 124–125° C.; $^1$H NMR δ 1.08 (s, 3H), 1.19 (s, 3H), 2.11 (s, 3H), 2.37 (d, J =17.4 Hz, 1H), 2.56 (d, J=17.4 Hz, 1H), 3.15 (m, 1H), 3.39 (m, 1H), 5.20 (m, 1H), 6.21 (m, 1H), 6.68 (m, 1H), 7.10 (m, 2H), 7.70

(m, 2H), 8.22 (br, 1H); $^{13}$C NMR δ 23.9, 24.2, 24.8, 31.6, 36.8, 51.2, 91.1, 94.2, 109.1, 117.8, 122.2, 122.4, 130.1, 135.9, 137.5, 206.7; FAB-MS obsd 440.0605, calcd 440.0597; Anal. Calcd for $C_{18}H_{21}IN_2O_3$: C, 49.1; H, 4.8; N, 6.4. Found: C, 49.1; H, 4.7; N, 6.3.

1,3,3-Trimethyl-7-(4-iodophenyl)-2,3-dihydrodipyrrin (21).

Following the procedure for a β-unsubstituted pyrrole (Strachan, J. P. et al., *J. Org. Chem.* 2000, 65, 3160–3172), a solution of 20 (220 mg, 0.50 mmol) in anhydrous THF (5.0 mL) under argon was treated with NaOMe (135 mg, 2.5 mmol) and the mixture was stirred for 1 h at room temperature (first flask). In a second flask, TiCl$_3$ (8.6 wt. % TiCl$_3$ in 28 wt. % HCl, 3.8 mL, 2.5 mmol, 5.0 mol equivalent) and H$_2$0 (20 mL) were combined, NH$_4$OAc (~15 g) was added to buffer the solution to pH 6.0, and then THF (5 mL) was added. The nitronate anion of 20 formed in the first flask was transferred via a cannula to the buffered TiCl$_3$ solution in the second flask. Additional THF (3 mL) was added to the nitronate anion flask and the supernatant was also transferred to the buffered TiCl$_3$ solution. The resulting mixture was stirred at room temperature for 6 h under argon. Then the mixture was extracted with ethyl acetate and the combined organic layers were washed with satd aq NaHCO$_3$, water, brine, and then dried (MgSO$_4$). The solvent was removed under reduced pressure at room temperature. The crude product was passed through a short column [alumina, hexanes/ethyl acetate (2:1)] to afford a light green solid (80–92 mg, 45–50%): mp 140–142° C.; $^1$H NMR δ 1.18 (s, 6H), 2.22 (s, 3H), 2.52 (s, 2H), 5.89 (s, 1H), 6.26 (m, 1H), 6.85 (m, 1H), 7.19 (m, 2H), 7.69 (m, 2H), 11.09 (br, 1H); 13C NMR δ20.7, 29.1, 29.7, 41.2, 53.7, 90.3, 102.3, 108.6, 118.5, 122.2, 127.5, 130.4, 136.8, 137.4, 161.9, 177.2; FAB-MS obsd 390.0595, calcd 390.0593 ($Cl_{18}H_{19}IN_2$); $\lambda_{abs}$ (toluene) 352 nm.

General Procedure for Chlorin Formation: Zn(II)-17,18-Dihydro-18,18-dimethyl-5-(4-methylphenyl)-12-(4-iodophenyl)porphyrin (Zn-22).

Following a general procedure (Strachan, J. P. et al., *J. Org. Chem.* 2000, 65, 3160–3172), to a solution of 11 (110 mg, 0.20 mmol) in 7.5 mL of anhydrous THF/MeOH (4:1) at room temperature was added excess of NaBH4 (100 mg, 2.6 mmol) in small portions. The reaction was monitored by TLC [alumina, hexanes/ethyl acetate (3:1)] and upon completion the mixture was quenched with cold water (~10 mL), then extracted with distilled CH$_2$Cl$_2$ (3×25 mL). The combined organic layers were washed with brine (50 mL), dried (K$_2$CO$_3$) for 2–3 min, and concentrated in vacuo at room temperature to leave the resulting carbinol 11-OH in ~1–2 mL of CH$_2$Cl$_2$. The WH 1 (45 mg, 0.24 mmol) was dissolved in a few mL of anhydrous CH$_3$CN and combined with 11-OH, then additional anhydrous CH$_3$CN was added to give a total of 22 mL CH$_3$CN. The solution was stirred at room temperature under argon and TFA (20 μL, 0.26 mmol) was added. The reaction was monitored by TLC [alumina, hexanes/ethyl acetate (3:1)], which after 25–30 min showed the disappearance of the EH and the appearance of a bright spot just below the WH. The reaction mixture was quenched with 10% aq NaHCO$_3$ and extracted with distilled CH$_2$Cl$_2$ (3×25 mL). The combined organic layers were washed with water, brine, dried (Na$_2$SO$_4$) and the solvent was removed in vacuo at room temperature. The residue was dissolved in 14 mL of anhydrous toluene under argon, then AgIO$_3$ (848 mg, 3.0 mmol), piperidine (300 μL, 3.0 mmol) and Zn(OAc)$_2$ (550 mg, 3.0 mmol) were added. The resulting mixture was heated at 80° C. for 2.5 h. The reaction was monitored by TLC [silica, hexanes/CH$_2$Cl$_2$, (1:1); showing a single green spot)] and absorption spectroscopy (bands at ~410 nm and ~610 nm). The color change of the reaction mixture from red to green indicates the formation of chlorin. The reaction mixture was cooled to room temperature then passed through a short column (silica, CH$_2$Cl$_2$). The major fraction was concentrated and again chromatographed [silica, hexanes/CH$_2$Cl$_2$ (2:1 then 1:1)]. The greenish blue solid obtained was dissolved in a minimum of CH$_2$Cl$_2$ and precipitated by adding hexanes, affording a greenish blue solid (25 mg, 18%). $^1$H NMR δ 2.01 (s, 6H), 2.67 (s, 3H), 4.48 (s, 2H), 7.50 (d, J=7.2 Hz, 2H), 7.91 (d, J=7.2 Hz, 2H), 7.95 (d, J=8.1 Hz, 2H), 8.09 (d,J=8.1 Hz, 2H), 8.51 (d, J=4.2 Hz, 1H), 8.67 (m, 5H), 8.78 (d, J=4.2 Hz, 1H), 9.56 (s, 1H); LD-MS obsd 693.78; FAB-MS obsd 694.0580, calcd 694.0572 ($C_{35}H_{27}IN_4Zn$); $\lambda_{abs}$ (toluene)/nm 411 (log ε=5.33, fwhm=18 nm), 616 (4.76), $\lambda_{em}$ 619, 674 nm.

Notes About Chlorin Formation.

(1) The complete reduction of the carbonyl in the EH precursor to the corresponding carbinol sometimes requires additional NaBH$_4$. The reduction must be complete prior to performing the chlorin forming reaction. (2) Upon workup of the EH the organic layers were dried in K$_2$CO$_3$ (the carbinol decomposes quickly upon drying over Na$_2$SO$_4$ or MgSO$_4$). It is important to not take the EH solution to dryness, as the EH in dried form is quite labile. (3) The EH upon workup, and the condensation solution giving the dihydrobilene-α, generally were either yellow or light red; these solutions led to chlorins in good yield. In some instances, further darkening was observed, in which case low yields of chlorins were obtained.

General Conditions for Demetalation.

17,18-Dihydro-18,18-dimethyl-5-(4-methylphenyl)-12-(4-iodophenyl)porphyrin (22).

To a solution of Zn-22 (10 mg, 14.4 μmol) in anhydrous CH$_2$Cl$_2$ (5 mL) was added TFA (58 μL, 0.75 mmol). After stirring for 30 min at room temperature (monitoring by TLC and UV-Visible spectroscopy), the reaction was quenched with 10% aq NaHCO$_3$ (20 mL) and extracted with CH$_2$Cl$_2$. The combined organic layers were washed with water, dried (Na$_2$SO$_4$), and concentrated. Further purification (if necessary) was achieved by chromatography on a short column [silica, hexanes/CH$_2$Cl$_2$ (1:1 then 1:2)] affording a green solid (8.0 mg, 88%). $^1$H NMR δ −2.15 (br, 1H), −1.85 (br, 1H), 2.07 (s, 6H), 2.69 (s, 3H), 4.64 (s, 2H), 7.54 (d, J=7.5 Hz, 2H), 8.04 (m, 4H), 8.16 (d, J=8.1 Hz, 2H), 8.64 (d, J=4.5 Hz, 1H), 8.85 (AB quartet, J=4.5 Hz, 2H), 8.90 (m, 3H), 8.99 (s, 1H), 9.84 (s, 1H); LD-MS obsd 633.88; FAB-MS obsd 632.1434, calcd 632.1437 ($C_{35}H_{29}IN_4$); $\lambda_{abs}$ (toluene)/nm 414 (log ε=5.13, fwhm=34 nm), 505 (4.12), 643 (4.65); $\lambda_{em}$ 646, 682 nm.

Zn(II)-17,18-Dihydro-18,18-dimethyl-5-(4-methylphenyl)-12-{4-[2-(trimethylsilyl)ethynyl]phenyl}porphyrin (Zn-23).

Following the general procedure for chlorin formation, the reaction of 13-OH [prepared from 13 (130 mg, 0.25 mmol)] and 1 (57 mg, 0.30 mmol) yielded a blue solid (36 mg, 22%). $^1$H NMR 6 0.35 (s, 9H), 2.03 (s, 6H), 2.67 (s, 3H), 4.54 (s, 2H), 7.50 (d, J=8.1 Hz, 2H), 7.86 (d, J=8.1 Hz, 2H), 7.96 (d, J=7.5 Hz, 2H), 8.16 (d, J=8.1 Hz, 2H), 8.53 (d, J=4.5 Hz, 1H), 8.60 (s, 1H), 8.68 (m, 2H), 8.73 (d, J=4.5 Hz, 1H), 8.75 (s, 1H), 8.80 (d, J=4.5 Hz, 1H), 9.63 (s, 1H); LD-MS obsd 665.74; FAB-MS obsd 664.2007, calcd 664.2001; ($C_{40}H_{36}IN_4SiZn$); $\lambda_{abs}$ (toluene)/nm 413 (log ε=5.31, fwhm =21 nm), 618 (4.77), $\lambda_{em}$ 622, 676 nm ($\Phi_f$=0.11).

17,18-Dihydro-18,18-dimethyl-5-(4-methylphenyl)-12-{4-[2-(trimethylsilyl)ethynyl]phenyl}porphyrin (23).

Following the general demetalation procedure, a sample of Zn-23 (10 mg, 15 μmol) gave a green solid (8.0 mg, 89%).

¹H NMR δ -2.15 (br, 1H), -1.85 (br, 1H), 0.35 (s, 9H), 2.07 (s, 6H), 2.69 (s, 3H), 4.64 (s, 2H), 7.53 (d, J=7.5 Hz, 2H), 7.91 (d, J=8.1 Hz, 2H), 8.03 (d, J=8.1 Hz, 2H), 8.27 (d, J=8.1 Hz, 2H), 8.64 (d, J=4.5 Hz, 1H), 8.84 (AB quartet, J=4.5 Hz, 2H), 8.89 (m, 2H), 8.93 (s, 1H), 8.99 (s, 1H), 9.86 (s, 1H); LD-MS obsd 604.31; FAB-MS obsd 602.2880, calcd 602.2866 ($C_{40}H_{38}IN_4Si$); $\lambda_{abs}$ (toluene)/nm 415 (log ε=4.97, fwhm=36 nm), 506 (3.96), 647 (4.49); $\lambda_{em}$ 648, 685, 715 nm ($\Phi_f$=0.25).

Zn(II)-17,18-Dihydro-18,18-dimethyl-5-(4-methylphenyl)-8-(4-iodophenyl)porphyrin (Zn-24).

Following the general procedure for chlorin formation, the reaction of 17-OH [prepared from 17 (110 mg, 0.20 mmol)] and 1 (45 mg, 0.24 mmol) yielded a blue solid (30 mg, 24%). ¹H NMR δ 2.03 (s, 6H), 2.67 (s, 3H), 4.51 (s, 2H), 7.50 (d, J=8.1 Hz, 2H), 7.86 (d, J=8.1 Hz, 2H), 7.97 (d, J=8.1 Hz, 2H), 8.02 (d, J=8.1 Hz, 2H), 8.54 (s, 1H), 8.60 (s, 1H), 8.69 (m, 4H), 8.97 (d, J=4.2 Hz, 1H), 9.61 (s, 1H); LD-MS obsd 696.39; FAB-MS obsd 694.0607, calcd 694.0572 ($C_{35}H_{27}IN_4Zn$); $\lambda_{abs}$ (toluene)/nm 416 (log ε=5.13,fwhm=18 nm), 607 (4.49); $\lambda_{em}$ 609, 661 nm.

17,18-Dihydro-18,18-dimethyl-5-(4-methylphenyl)-8-(4-iodophenyl)porphyrin (24).

Following the general demetalation procedure, a sample of Zn-24 (10 mg, 14.4 μmol) gave a green solid (7.5 mg, 83%). ¹H NMR δ -2.20 (br, 1H), -1.96 (br, 1H), 2.07 (s, 6H), 2.68 (s, 3H), 4.63 (s, 2H), 7.53 (d, J=8.1 Hz, 2H), 7.86 (d, J=8.7 Hz, 2H), 8.03 (m, 4H), 8.64 (s, 1H), 8.85 (m, 3H), 8.91 (s, 1H), 8.99 (s, 1H), 9.17 (d, J=4.5 Hz, 1H), 9.83 (s, 1H); LD-MS obsd 631.58; FAB-MS obsd 632.1454, calcd 632.1437 ($C_{35}H_{29}IN_4$); $\lambda_{abs}$ (toluene)/nm 410 (log ε=5.11, fwhm 32 nm), 504 (4.01), 638 (4.48); $\lambda_{em}$ 639, 679, 702 nm.

Zn(II)-17,18-Dihydro-18,18-dimethyl-2-(4-iodophenyl)-5-(4-methylphenyl)-12-{4-[2-(trimethylsilyl)ethynyl]phenyl}porphyrin (Zn-25).

Following the general procedure for chlorin formation, the reaction of 13-OH [prepared from 13 (103 mg, 0.20 mmol)] and 21 (86 mg, 0.22 mmol) yielded a blue solid (42 mg, 24%). ¹H NMR δ 0.36 (s, 9H), 1.96 (s, 6H), 2.67 (s, 3H), 4.48 (s, 1H), 7.50 (d, J=7.5 Hz, 2H), 7.82 (d, J=8.7 Hz, 2H), 7.86 (d, J=8.1 Hz, 2H), 7.97 (d, J =8.1 Hz, 2H), 8.02 (d, J=8.1 Hz, 2H), 8.13 (d, J=7.8 Hz, 2H), 8.51 (d, J=4.2 Hz, 1H), 8.63 (s, 1H), 8.67 (s, 1H), 8.70 (s, 2H), 8.78 (d, J=4.2 Hz, 1H), 9.58 (s, 1H); LD-MS 866.34; FAB-MS obsd 866.1257, calcd 866.1280 ($C_{46}H_{39}IN_4SiZn$); $\lambda_{abs}$ (toluene)/nm 417 (log ε=5.32, fwhm=21 nm), 629 (4.90); $\lambda_{em}$ 635, 691 nm.

17,18-Dihydro-18,18-dimethyl-2-(4-iodophenyl)-5-(4-methylphenyl)-12-{4-12-(trimethylsilyl)ethynyllphenyl}porphyrin (25).

Following the general demetalation procedure, a sample of Zn-25 (11.0 mg, 13.7 μmol) gave a green solid (8.0 mg, 78%). ¹H NMR δ -1.95 (br, 1H), -1.70 (br, 1H), 0.36 (s, 9H), 2.0 (s, 6H), 2.68 (s, 3H), 4.60 (s, 2H), 7.53 (d, J=8.1 Hz, 2H), 7.91 (d, J=8.1 Hz, 2H), 8.03 (d, J =8.1 Hz, 2H), 8.07 (d, J=8.1 Hz, 2H), 8.26 (d, J=8.1 Hz, 2H), 8.62 (d, J=4.2 Hz, 1H), 8.81 (s, 1H), 8.88 (d, J=4.2 Hz, 1H), 8.91 (s, 1H), 8.95 (s, 1H), 8.96 (s, 1H), 9.84 (s, 1H); LD-MS 804.02; FAB-MS obsd 804.2157, calcd 804.2145 ($C_{46}H_{41}IN_4Si$); $\lambda_{abs}$ (toluene)/nm 422 (log ε=5.09, fwhm=34 nm), 509 (4.08), 655 (4.68); $\lambda_{em}$ 660, 726 nm.

TABLE 1

Absorption spectral properties of chlorins.[a]

| Chlorins | $\lambda_{max}$ (nm), Soret | $\lambda_{max}$ (nm), Q | Soret/Q intensity ratio |
|---|---|---|---|
| 24 | 409 | 637 | 4.3 |
| 22 | 414 | 643 | 3.0 |
| 23 | 416 | 645 | 3.1 |
| 25 | 422 | 655 | 2.5 |
| Pheophytin a[b] | 408 | 667 | 2.1 |
| Pheophytin b[b] | 434 | 655 | 5.1 |
| Zn-24 | 415 | 606 | 4.3 |
| Zn-22 | 411 | 615 | 3.6 |
| Zn-23 | 412 | 617 | 3.5 |
| Zn-25 | 417 | 628 | 2.6 |
| Chlorophyll a[b] | 430 | 662 | 1.3 |
| Chlorophyll b[b] | 455 | 644 | 2.8 |

[a]In toluene at room temperature.
[b]In diethyl ether (Smith, J. H. C.; Benitez, A. In Modern Methods of Plant Analysis, Paech, K.; Tracey, M. V., Eds.; Springer-Verlag: Berlin 1955, Vol. IV, pp. 142–196).

An alternative approach to chlorins that bear a geminal dimethyl lock, avoid flanking meso and β substituents, and can be used in model systems has involved reaction of a tripyrrole complex with a pyrrole finctionalized for subsequent elaboration (Montforts, F. -P.; Kutzki, O. Angew. Chem. Int. Ed. 2000, 39, 599–601; Abel, and Montforts, F. -P. Tetrahedron Lett. 1997, 38, 1745–1748: Schmidt, W.; Montforts, F. -P. Synlett 1997, 903–904).

The foregoing is illustrative of the present invention, and is not to be construed as limiting thereof. The invention is defined by the following claims, with equivalents of the claims to be included therein.

What is claimed is:

1. A trans-substituted chlorin comprising a compound of Formula X:

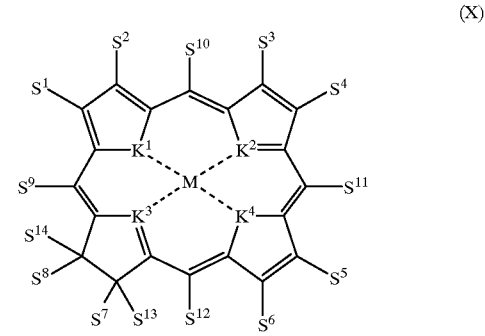

(X)

wherein:
M is a metal selected from the group consisting of Zn, Mg, Pt, Pd, Sn and Al;
$K^1$, $K^2$, $K^3$, and $K^4$ are hetero atoms independently selected from the group consisting of N, O, S, Se, Te, and CH;
$S^3$, $S^4$, $S^7$, $S^8$, $S^9$, $S^{10}$, $S^{11}$, $S^{12}$, $S^{13}$, and $S^{14}$, and either $S^1$ and $S^5$, or $S^2$ and $S^6$ are independently selected from the group consisting of H, aryl, phenyl, cycloalkyl, alkyl, alkenyl, alkynyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl;
or $S^7$ and $S^{13}$ together form =O;
and either $S^1$ and $S^5$ are trans-substituted linking groups $Q^1$ and $Q^2$, or $S^2$ and $S^6$ are trans-substituted linking groups $Q^1$ and $Q^2$;

$Q^1$ and $Q^2$ are independently selected linking groups of the formula:

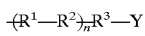

wherein:

n is from 0 or 1 to 5 or 10;

$R^3$ is present or absent;

$R^1$, $R^2$, and $R^3$ are each independently selected from the group consisting of ethene, ethyne, aryl, and heteroaryl groups, which aryl and heteroaryl groups are unsubstituted or substituted one or more times with H, aryl, phenyl, cycloalkyl, alkyl, alkenyl, alkynyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl; and Y is a protected or unprotected reactive substituent selected from the group consisting of hydroxy, thio, seleno, telluro, ester, carboxylic acid, boronic acid, phenol, silane, sulfonic acid, phosphonic acid, alkylthiol, formyl, halo, alkenyl, alkynyl, haloalkyl, alkyl phosphonate, alkyl sulfonate, alkyl carboxylate, and alkyl boronate groups.

2. A compound according to claim 1, wherein $S^1$ and $S^5$ are trans-substituted linking groups $Q^1$ and $Q^2$.

3. A compound according to claim 1, wherein $S^2$ and $S^6$ are trans-substituted linking groups $Q^1$ and $Q^2$.

4. A compound according to claim 1, wherein M is Zn or Mg.

5. A compound according to claim 1, wherein $K^1$, $K^2$, $K^3$, and $K^4$ are independently selected from the group consisting of N, O, S, and CH.

6. A compound according to claim 1, wherein $K^1$, $K^2$, $K^3$, and $K^4$ are all N.

7. A compound according to claim 1, wherein $S^4$, $S^7$, $S^8$, $S^9$, $S^{10}$, $S^{11}$, $S^{12}$, $S^{13}$, and $S^{14}$ are all alkyl.

8. A method of making a trans-substituted chlorin according to claim 1, comprising the steps of:

(a) condensing a compound of formula WH with a compound of formula EH in an organic solvent in the presence of an acid to form a condensation product;

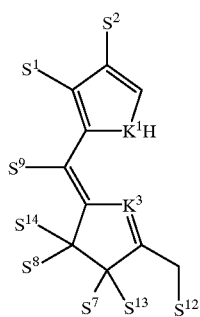

WH

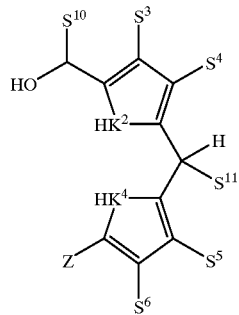

EH wherein Z is selected from the group consisting of halo, alkoxy, and acetoxy; and then (b) oxidatively cyclizing said condensation product in an organic solvent in the presence of a base, an oxidant and a metal salt $MX'_t$, where M is as defined above, X' is an anion and t is 2–3, to produce a compound of Formula X above.

9. A method according to claim 8, wherein said acid is a Bronsted or Lewis acid.

10. A method according to claim 8, wherein said organic solvent is a polar solvent.

11. A method according to claim 8, wherein said organic solvent is a nonpolar solvent.

12. A method according to claim 8, wherein said organic solvent is a protic solvent.

13. A method according to claim 8, wherein said organic solvent is an aprotic solvent.

14. A method according to claim 8, wherein said base is piperidine.

15. A method according to claim 8, wherein said oxidant is silver iodate or oxygen.

16. A method according to claim 8, wherein Z is Br.

17. A polymer comprising at least three monomers, each of said monomers comprising a porphyrinic macrocycle, wherein at least one of said porphyrinic macrocycles is a chlorin, and wherein said chlorin is:

(i) coupled to two adjacent porphyrinic macrocycles in said polymer at the 2 and 12 positions; or (ii) coupled to two adjacent porphyrinic macrocycles in said polymer at the 3 and 13 positions.

18. A polymer according to claim 17 consisting essentially of 2 to 200 porphyrinic macrocycle monomers.

19. A polymer according to claim 17 consisting essentially of 3 to 50 porphyrinic macrocycle monomers.

20. A polymer according to claim 17, wherein at least 2 of said porphyrinic macrocycles is an independently selected chlorin, and wherein each of said independently selected chlorins is:

(i) coupled to one or two adjacent porphyrinic macrocycles in said polymer at the 2 position, the 12 position, or the 2 and 12 positions; or (ii) coupled to one or two adjacent porphyrinic macrocycles in said polymer at the 3 position, the 13 position, or the 3 and 13 positions.

21. A polymer according to claim 17, wherein each of said porphyrinic macrocycles is an independently selected chlorin, and wherein each of said independently selected chlorins is:

(i) coupled to one or two adjacent porphyrinic macrocycles in said polymer at the 2 position, the 12 position, or the 2 and 12 positions; or (ii) coupled to one or two adjacent porphyrinic macrocycles in said polymer at the 3 position, the 13 position, or the 3 and 13 positions.

22. A polymer according to claim 17, wherein said chiorin has Formula X:

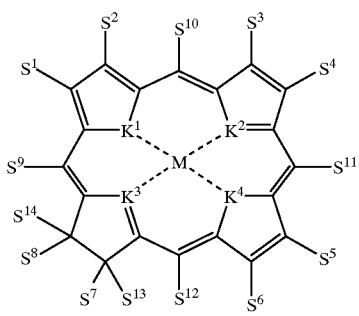

(X)

wherein:

M is a metal selected from the group consisting of Zn, Mg, Pt, Pd, Sn and Al, or M is absent;

$K^1$, $K^2$, $K^3$, and $K^4$ are hetero atoms independently selected from the group consisting of N, O, S, Se, Te, and CH;

$S^1$, $S^2$, $S^3$, $S^4$, $S^5$, $S^6$, $S^7$, $S^8$, $S^9$, $S^{10}$, $S^{11}$, $S^{12}$, $S^{13}$, and $S^{14}$ are independently selected from the group consisting of H, aryl, phenyl, cycloalkyl, alkyl, alkenyl, alkynyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl;

or $S^7$ and $S^{13}$ together form =O;

and subject to the proviso that said compound of Formula X is:

(i) coupled by a linking group to two adjacent porphyrinic macrocycles in said polymer at the $S^1$ position, the $S^5$ position, or the $S^1$ and $S^5$ positions; or (ii) coupled by a linking group to two adjacent porphyrinic macrocycles in said polymer at the $S^2$ position, the $S^6$ position, or the $S^2$ and $S^6$ positions.

23. An electrode comprising a conductive substrate having a polymer bound thereto, said polymer comprising a plurality of monomers, each of said monomers comprising a porphyrinic macrocycle, wherein at least one of said porphyrinic macrocycles is a chlorin, and wherein said chlorin is:

(i) coupled to one or two adjacent porphyrinic macrocycles in said polymer at the 2 position, the 12 position, or the 2 and 12 positions; or (ii) coupled to one or two adjacent porphyrinic macrocycles in said polymer at the 3 position, the 13 position, or the 3 and 13 positions.

24. An electrode according to claim 23 wherein said chlorin is coupled to one adjacent porphyrinic macrocycle in said polymer at the 2 position or the 12 position.

25. An electrode according to claim 23 wherein said chlorin is coupled to two adjacent porphyrinic macrocycles at the 2 and 12 positions.

26. An electrode according to claim 23 wherein said chlorin is coupled to one adjacent porphyrinic macrocycle in said polymer at the 3 position or the 13 position.

27. An electrode according to claim 23 wherein said chlorin is coupled to two adjacent porphyrinic macrocycles at both the 3 and 13 positions.

28. An electrode according to claim 23 wherein the polymer consists essentially of 2 to 200 porphyrinic macrocycle monomers.

29. An electrode according to claim 23 wherein the polymer consists essentially of 3 to 50 porphyrinic macrocycle monomers.

30. An electrode according to claim 23, wherein at least 2 of said porphyrinic macrocycles is an independently selected chiorin, and wherein each of said independently selected chlorins is:

(i) coupled to one or two adjacent porphyrinic macrocycles in said polymer at the 2 position, the 12 position, or the 2 and 12 positions; or (ii) coupled to one or two adjacent porphyrinic macrocycles in said polymer at the 3 position, the 13 position, or the 3 and 13 positions.

31. An electrode according to claim 23, wherein each of said porphyrinic macrocycles is an independently selected chiorin, and wherein each of said independently selected chlorins is:

(i) coupled to one or two adjacent porphyrinic macrocycles in said polymer at the 2 position, the 12 position, or the 2 and 12 positions; or (ii) coupled to one or two adjacent porphyrinic macrocycles in said polymer at the 3 position, the 13 position, or the 3 and 13 positions.

32. An electrode according to claim 23, wherein said chlorin has Formula X:

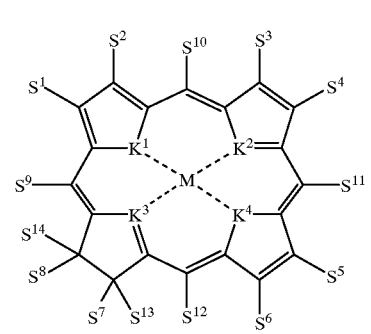

(X)

wherein:

M is a metal selected from the group consisting of Zn, Mg, Pt, Pd, Sn and Al, or M is absent;

$K^1$, $K^2$, $K^3$, and $K^4$ are hetero atoms independently selected from the group consisting of N, O, S, Se, Te, and CH;

$S^1$, $S^2$, $S^3$, $S^4$, $S^5$, $S^6$, $S^7$, $S^8$, $S^9$, $S^{10}$, $S^{11}$, $S^{12}$, $S^{13}$, and $S^{14}$ are independently selected from the group consisting of H, aryl, phenyl, cycloalkyl, alkyl, alkenyl, alkynyl, halogen, alkoxy, alkylthio, perfluoroalkyl, perfluoroaryl, pyridyl, cyano, thiocyanato, nitro, amino, alkylamino, acyl, sulfoxyl, sulfonyl, imido, amido, and carbamoyl;

or $S^7$ and $S^{13}$ together form =O;

and subject to the proviso that said compound of Formula X is:

(i) coupled by a linking group to one or two adjacent porphyrinic macrocycles in said polymer at the $S^1$ position, the $S^5$ position, or the $S^1$ and $S^5$ positions; or (ii) coupled by a linking group to one or two adjacent porphyrinic macrocycles in said polymer at the $S^2$ position, the $S^6$ position, or the $S^2$ and $S^6$ positions.

* * * * *